US009688703B2

(12) United States Patent
Coppernoll et al.

(10) Patent No.: US 9,688,703 B2
(45) Date of Patent: Jun. 27, 2017

(54) METHOD FOR PREPARING A HALOSILANE

(71) Applicant: Dow Corning Corporation, Midland, MI (US)

(72) Inventors: Aaron Coppernoll, Crestwood, KY (US); Krishna Janmanchi, Union, KY (US); Catharine Horner, Carrollton, KY (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 15/026,272

(22) PCT Filed: Oct. 30, 2014

(86) PCT No.: PCT/US2014/063044
§ 371 (c)(1),
(2) Date: Mar. 31, 2016

(87) PCT Pub. No.: WO2015/073213
PCT Pub. Date: May 21, 2015

(65) Prior Publication Data
US 2016/0244468 A1 Aug. 25, 2016

Related U.S. Application Data

(60) Provisional application No. 61/902,823, filed on Nov. 12, 2013.

(51) Int. Cl.
| C07F 7/02 | (2006.01) |
| C07F 7/14 | (2006.01) |
| B01J 23/00 | (2006.01) |
| B01J 23/72 | (2006.01) |
| B01J 23/745 | (2006.01) |
| B01J 23/89 | (2006.01) |
| B01J 37/08 | (2006.01) |
| C08G 77/06 | (2006.01) |
| C07F 7/12 | (2006.01) |

(52) U.S. Cl.
CPC .............. C07F 7/14 (2013.01); B01J 23/005 (2013.01); B01J 23/72 (2013.01); B01J 23/745 (2013.01); B01J 23/8993 (2013.01); B01J 37/08 (2013.01); C07F 7/12 (2013.01); C08G 77/06 (2013.01); C07F 7/122 (2013.01); Y02P 20/582 (2015.11)

(58) Field of Classification Search
CPC .................................. C08F 7/12; C08F 7/122
See application file for complete search history.

(56) References Cited

U.S. PATENT DOCUMENTS

| 2,380,996 A | 8/1945 | Rochow et al. |
| 2,403,370 A | 7/1946 | Hurd |
| 2,406,605 A | 8/1946 | Hurd |
| 2,458,703 A | 1/1949 | Hatcher |
| 2,595,620 A | 5/1952 | Wagner et al. |
| 2,851,473 A * | 9/1958 | Wagner ..................... C07F 7/14 528/15 |
| 2,888,476 A | 5/1959 | Little et al. |
| 3,057,686 A | 10/1962 | Muetterties |
| 4,053,495 A | 10/1977 | Deinhammer et al. |
| 4,059,608 A | 11/1977 | Calas et al. |
| 4,079,071 A | 3/1978 | Neale |
| 4,314,908 A | 2/1982 | Downing et al. |
| 4,500,724 A | 2/1985 | Ward et al. |
| 4,526,769 A | 7/1985 | Ingle et al. |
| 4,602,101 A | 7/1986 | Halm et al. |
| 4,631,266 A | 12/1986 | Wold et al. |
| 4,836,997 A | 6/1989 | Lepage et al. |
| 4,864,044 A | 9/1989 | Lewis et al. |
| 4,888,435 A | 12/1989 | Chadwick et al. |
| 4,889,838 A * | 12/1989 | Lewis ..................... C07F 7/125 423/342 |
| 4,946,980 A | 8/1990 | Halm et al. |

(Continued)

FOREIGN PATENT DOCUMENTS

| CN | 1209823 A | 3/1999 |
| CN | 1403372 A | 3/2003 |
| CN | 102068988 A | 5/2011 |
| DE | 3024319 | 1/1982 |
| DE | 4041644 A1 | 6/1992 |
| DE | 19654154 | 6/1997 |
| EP | 0146148 A1 | 6/1985 |
| EP | 0365207 B1 | 2/1995 |
| FR | 2879477 A1 | 6/2006 |
| JP | S28-000669 | 2/1953 |
| JP | 2009111202 | 5/2009 |
| JP | 4607715 B2 | 1/2011 |
| WO | 2010149286 A1 | 12/2010 |
| WO | 2014028417 A2 | 2/2014 |
| WO | 2014062255 A1 | 4/2014 |

OTHER PUBLICATIONS

Hurd, et. al., "The Vapor Phase Alkylation and Hydrogenation of Chlorosilanes", J. Am. Chem. Soc., 1945, 67 (9), pp. 1545-1548.

(Continued)

*Primary Examiner* — Margaret Moore
(74) *Attorney, Agent, or Firm* — Catherine U. Brown

(57) ABSTRACT

A method for preparing a reaction product includes: steps (1) and (2). Step (1) is contacting, at a temperature from 200° C. to 1400° C., a first ingredient including a silane of formula $H_aR_bSiX_{(4-a-b)}$, where subscript a is an integer from 0 to 4, subscript b is 0 or 1, a quantity (a+b)<4, each R is independently a monovalent organic group, and each X is independently a halogen atom, with the proviso that when the quantity (a+b)<4, then the ingredient further includes H2; with a spinel catalyst including copper; thereby forming a reactant. Step (2) is contacting the reactant with a second ingredient including an organohalide at a temperature from 100° C. to 600° C.; thereby forming the reaction product and a spent reactant. The reaction product is distinct from the silane used in step (1). The method may be used to prepare diorganodihalosilanes from silicon tetrahalides.

20 Claims, No Drawings

(56) References Cited

U.S. PATENT DOCUMENTS

| | | | |
|---|---|---|---|
| 4,956,326 | A | 9/1990 | Yoneda et al. |
| 4,973,725 | A | 11/1990 | Lewis et al. |
| 4,985,580 | A | 1/1991 | Chadwick et al. |
| 5,336,799 | A | 8/1994 | Kalchauer et al. |
| 5,646,326 | A | 7/1997 | Schuler |
| 5,716,590 | A | 2/1998 | Roewer et al. |
| 6,156,380 | A | 12/2000 | Aramata et al. |
| 6,211,284 | B1 | 4/2001 | Ishikawa et al. |
| 6,251,057 | B1 | 6/2001 | Jung et al. |
| 6,288,258 | B1* | 9/2001 | Aramata ............ C07F 7/16 556/472 |
| 6,326,452 | B1 | 12/2001 | Berrier et al. |
| 6,506,923 | B2 | 1/2003 | Inukai et al. |
| 6,576,588 | B2 | 6/2003 | Ryu et al. |
| 6,632,956 | B2 | 10/2003 | Tsukuno et al. |
| 6,768,018 | B2 | 7/2004 | Furuya et al. |
| 6,790,749 | B2 | 9/2004 | Takemura et al. |
| 6,887,448 | B2 | 5/2005 | Block et al. |
| 7,056,484 | B2 | 6/2006 | Bulan et al. |
| 7,208,617 | B2 | 4/2007 | Gammie |
| 7,212,778 | B2 | 5/2007 | Hisakuni |
| 7,223,879 | B2 | 5/2007 | Buchwald et al. |
| 7,355,060 | B2 | 4/2008 | Ogawa et al. |
| 7,442,824 | B2 | 10/2008 | Paetzold et al. |
| 7,559,969 | B2 | 7/2009 | Sanjurjo et al. |
| 7,638,498 | B2 | 12/2009 | Escher et al. |
| 7,716,590 | B1 | 5/2010 | Nathan |
| 7,728,176 | B2 | 6/2010 | Masaoka et al. |
| 7,754,175 | B2 | 7/2010 | Bill, Jr. et al. |
| 8,124,809 | B2 | 2/2012 | Masaoka et al. |
| 8,519,207 | B2 | 8/2013 | Armbruester et al. |
| 8,697,900 | B2 | 4/2014 | Anderson et al. |
| 8,772,525 | B2 | 7/2014 | Katsoulis et al. |
| 8,962,877 | B2 | 2/2015 | Kohane et al. |
| 2002/0044904 | A1 | 4/2002 | Bulan et al. |
| 2003/0220514 | A1 | 11/2003 | Lewis et al. |
| 2004/0022713 | A1 | 2/2004 | Bulan et al. |
| 2005/0074387 | A1 | 4/2005 | Bulan et al. |
| 2006/0165580 | A1 | 7/2006 | Lipshutz |
| 2009/0035205 | A1 | 2/2009 | Bohmhammel et al. |
| 2009/0324477 | A1 | 12/2009 | Mizushima et al. |
| 2011/0158884 | A1 | 6/2011 | Bentley et al. |
| 2012/0289730 | A1* | 11/2012 | Anderson ............ C07F 7/16 556/450 |
| 2014/0178283 | A1 | 6/2014 | Schladerbeck et al. |
| 2014/0212352 | A1 | 7/2014 | Onal et al. |
| 2014/0303420 | A1 | 10/2014 | Holmes et al. |
| 2014/0322121 | A1 | 10/2014 | Dassel |
| 2015/0232488 | A1* | 8/2015 | Dash ............ C08G 77/60 528/31 |

OTHER PUBLICATIONS

Eaborn, et al., "Further studies on reactions of organic halides with disilanes catalysed by transition metal complexes", Journal of Organometallic Chemistry, vol. 225, 1982, pp. 331-341.
Golubstov, et al., "Role of the Products of Partial Chlorination of Silicon in the Formation of Methyltrichlorosilane", Russian Chemical Bulletin, vol. 21, No. 3 (1972), pp. 584-586.
Walter et. al., "Mechanism of the silicide-catalysed hydrodehalogenation of silicon tetrachloride to trichlorosilane", J. Chem. Soc., Faraday Trans., 1996, 92, pp. 4605-4608.
Juszczyk et al., "Transformation of Pd/SiO2 catalysts during high temperature reduction", Department of Catalysis on Metals, Institute of Physical Chemistry, Polish Academy of Sciences, Warsaw, Poland, Catalysis Letters 2002, 78(1-4), 95-98.
Juszczyk et al., "Transformation of Pd/SiO2 into palladium silicide during reduction at 450° and 500° C.", Institute of Physical Chemistry, Department of Catalysis on Metals, Polish Academy of Sciences, Warsaw, Poland, Journal of Catalysis, 2003, 220(2), 299-308.
Lobusevich, et al., "Reactions During Direct Synthesis of Alkylchlorosilanes", vol. 48, No. 11, 1978, pp. 2534-2541.
Moreno-Manas, et al., "Formation of Carbon-Carbon Bonds under Catalysis by Transition-Metal Nanoparticles", Department of Chemistry, Universitat Autonoma de Barcelona, Barcelona, Spain. Accounts of Chemical Research, 2003, 36(8), pp. 638-643.
Beccalli, et al., "C—C, C—O, C—N. Bond Formation on sp2 Carbon by Palladium(II)-Catalyzed Reactions Involving Oxidant Agents", Istituto di Chimica Organica A. Marchesini, Facolta di Farmacia, Universita di Milano, Milan, Italy. Chemical Reviews, Washington, DC, United States, 2007, 107(11), pp. 5318-5365.
Methivier, et al., "Pd/SiC catalysts. Characterization and catalytic activity for the methane total oxidation", Institut de Recherches sur la Catalyse-CNRS, conventionne a l'Universite Claude Bernard Lyon 1, Villeurbanne, France, Journal of Catalysis, 1998, 173(2), pp. 374-382.
Srebowata, et al., "Hydrodechlorination of 1,2-dichloroethane over differently reduced Pd/SiO2 catalysts", Institute of Physical Chemistry, Polish Academy of Sciences, Warsaw, Poland, Polish Journal of Chemistry, 2003, 77(12), pp. 1841-1848.
Tanaka, et al., "In-situo observation of Pd2Si islands on Si by UHV-TEM/STEM", Nanomaterials Laboratory, National Institute for Materials Science, Tsukuba, Sakura, Japan. Journal of Crystal Growth, 2002, pp. 237-239 (Pt. 1), and pp. 254-258.
Terao, et al., "Transition metal-catalyzed C—C bond formation reactions using alkyl halides", Department of Applied Chemistry and Center for Atomic and Molecular Technologies, Graduate School of Engineering, Osaka University, Osaka, Japan. Bulletin of the Chemical Society of Japan, 2006, 79(5), pp. 663-672.
Vijh, et al., "Discovery of some new stable electrocatalytic materials for the anodic oxidation of hydrazine", Inst. Rech. Hydro-Quebec, Varennes, QC, Cananda. Journal of Materials Science Letters, 1993, 12(2), pp. 113-115.
Vijh, et. al., "Electrochemical activity of silicides of some transition metals for the hydrogen evolution reaction in acidic solutions", International Journal of Hydrogen Energy, 1990, 15(11), pp. 789-794.
Yin, et. al., "Carbon-carbon coupling reactions catalyzed by heterogeneous palladium catalysts", Institute fuer Chemie, Humboldt-Universitaet Berlin, Berlin, Germany. Chemical Reviews, Washington, DC, United States, 2007, 107(1), pp. 133-173.
Mulla, et. al., "Reaction of Magnesium Silicide & Silicon Tetrachloride/Trichlorosilane in Presence of Hydrogen", Indian Journal of Chemistry, Sep. 1988, pp. 756-758, vol. 27A.
Acker, et. al., "Reactivity of Intermetallic Compounds: A Solid State Approach to Direct Reactions of Silicon", J. Phys. Chem., 2002, pp. 5105-5117, vol. 106, Freiberg, Germany.
Acker, et. al., "Thermodynamic assessment of the copper catalyzed direct synthesis of methylchlorosilanes", Journal of Organometallic Chemistry, 2008, pp. 2483-2493, vol. 693, Freiberg, Germany.
Ding, et. al., "CuCl-Catalyzed Hydrogenation of Silicon Tetrachloride in the Presence of Silicon: Mechanism and Kinetic Modeling", American Chemical Society, Industrial & Engineering Chemistry Research, Oct. 2, 2014, pp. AK, Shanghai, China.
Wu, Shengquan, "Comprehensive Use of Methyltrichlorosilane", Silicone Material, Jan. 22, 2000, vol. 14, Series 1, pp. 23-25. Abstract only.
Aijun, et al., Introduction of the Properties, Application and Production of Trichlorosilane, China Chlor-Alkali, Dec. 15, 2002, Series 12, pp. 40-41.
Jiang, et al., "Synthesis of Trimethylchlorosilane by [BMIM]Cl-nAlCl3 Ionic Liquids-Catalyzed Redistribution between Methyltrichlorosilane and Low-Boiling Products from the Direct Synthesis of Methylchlorosilanes", Ind. Eng. Chem. Res., Jan. 6, 2011, vol. 50, pp. 1893-1898.
Tan, et al., "Progress of Studies on the Comprehensive Utilization of Methyltrichlorosilane by Disproportionation and Transformation", Bulletin of Science and Technology, No. 2, vol. 22.

* cited by examiner

METHOD FOR PREPARING A HALOSILANE

CROSS REFERENCE TO RELATED APPLICATIONS

This application is a U.S. national stage filing under 35 U.S.C. §371 of PCT Application No. PCT/US14/063044 filed on 30 Oct. 2014, currently pending, which claims the benefit of U.S. Provisional Patent Application No. 61/902,823 filed Nov. 12, 2013 under 35 U.S.C. §119 (e). PCT Application No. PCT/US14/063044 and U.S. Provisional Patent Application No. 61/902,823 are hereby incorporated by reference.

Various halosilanes find use in different industries. Diorganodihalosilanes, such as dimethyldichlorosilane, are hydrolyzed to produce a wide range of polyorganosiloxanes, such as polydiorganosiloxanes.

Methods of preparing halosilanes are known in the art. Typically, halosilanes are produced commercially by the Mueller-Rochow Direct Process, which comprises passing a halide compound over zero-valent silicon ($Si^0$) in the presence of a copper catalyst and various optional promoters. Mixtures of halosilanes are produced by the Direct Process. When an organohalide is used, a mixture of organohalosilanes is produced by the Direct Process.

The typical process for making the $Si^0$ used in the Direct Process consists of the carbothermic reduction of $SiO_2$ in an electric arc furnace. Extremely high temperatures are required to reduce the $SiO_2$, so the process is energy intensive. Consequently, production of $Si^0$ adds costs to the Direct Process for producing halosilanes. Therefore, there is a need for a more economical method of producing halosilanes that avoids the need of using $Si^0$.

In addition to the Direct Process, diorganodihalosilanes have been produced by the alkylation of silicon tetrachloride and various methylchlorosilanes by passing the vapors of these chlorosilanes together with an alkyl halide over finely divided aluminum or zinc at elevated temperatures. However, this process results in the production of a large amount of aluminum chloride or zinc chloride, which is costly to dispose of on a commercial scale.

Therefore, there is a need for a more economical method of producing halosilanes that avoids the need for $Si^0$ produced by reducing $SiO_2$ at extremely high temperatures and that does not require the costly disposal of byproducts.

BRIEF SUMMARY OF THE INVENTION

A method for preparing a reaction product comprising a halosilane comprises:

step (1) contacting, at a temperature from 200° C. to 1400° C., a first ingredient comprising a silane of formula $H_aR_bSiX_{(4-a-b)}$, where subscript a is an integer from is 0 to 4, subscript b is 0 or 1, a quantity (a+b)≤4, each R is independently a monovalent organic group, and each X is independently a halogen atom, with the proviso that when the quantity (a+b) is <4, then the ingredient further comprises $H_2$; and a spinel catalyst comprising copper; thereby forming a reactant; and step (2) contacting the reactant and a second ingredient comprising an organohalide, and optionally hydrogen and/or a hydridohalide, at a temperature from 100° C. to 600° C.; thereby forming the reaction product and a spent reactant.

DETAILED DESCRIPTION OF THE INVENTION

The Brief Summary of the Invention and the Abstract are hereby incorporated by reference. All ratios, percentages, and other amounts are by weight, unless otherwise indicated. The articles 'a', 'an', and 'the' each refer to one or more, unless otherwise indicated by the context of the specification. Abbreviations used herein are defined in Table 1, below.

TABLE 1

Abbreviations

| Abbrev. | Word |
|---|---|
| % | Percent |
| Bu | "Bu" means butyl and includes branched and linear structures such as iso-butyl and, n-butyl. |
| ° C. | degrees Celsius |
| cm | Centimeters |
| Et | Ethyl |
| GC | gas chromatograph and/or gas chromatography |
| h | Hours |
| ICP-AES | inductively coupled plasma atomic emission spectroscopy |
| ICP-MS | inductively coupled plasma mass spectrometry |
| kPa | kiloPascals |
| L | Liters |
| Me | Methyl |
| mg | Milligram |
| min | Minutes |
| mL | Milliliters |
| Ph | Phenyl |
| Pr | "Pr" means propyl and includes branched and linear structures such as iso-propyl and, n-propyl. |
| s | Seconds |
| sccm | standard cubic centimeters per minute |
| Vi | Vinyl |
| XRD | X-ray diffraction |

"Alkyl" means an acyclic, branched or unbranched, saturated monovalent hydrocarbon group. Examples of alkyl groups include Me, Et, Pr, 1-methylethyl, Bu, 1-methylpropyl, 2-methylpropyl, 1,1-dim ethylethyl, 1-methylbutyl, 1-ethylpropyl, pentyl, 2-methylbutyl, 3-methylbutyl, 1,2-dimethylpropyl, 2,2-dimethylpropyl, hexyl, heptyl, 2-ethylhexyl, octyl, nonyl, and decyl; and as well as other branched saturated monovalent hydrocarbon groups with 6 or more carbon atoms. Alkyl groups have at least one carbon atom. Alternatively, alkyl groups may have 1 to 12 carbon atoms, alternatively 1 to 10 carbon atoms, alternatively 1 to 6 carbon atoms, alternatively 1 to 4 carbon atoms, alternatively 1 to 2 carbon atoms, and alternatively 1 carbon atom.

"Aralkyl" and "alkaryl" each refer to an alkyl group having a pendant and/or terminal aryl group or an aryl group having a pendant alkyl group. Exemplary aralkyl groups include benzyl, tolyl, xylyl, phenylethyl, phenyl propyl, and phenyl butyl. Aralkyl groups have at least 7 carbon atoms. Monocyclic aralkyl groups may have 7 to 12 carbon atoms, alternatively 7 to 9 carbon atoms, and alternatively 7 to 8 carbon atoms. Polycyclic aralkyl groups may have 7 to 17 carbon atoms, alternatively 7 to 14 carbon atoms, and alternatively 9 to 10 carbon atoms.

"Alkenyl" means an acyclic, branched, or unbranched unsaturated monovalent hydrocarbon group, where the monovalent hydrocarbon group has a double bond. Alkenyl groups include Vi, allyl, propenyl, and hexenyl. Alkenyl groups have at least 2 carbon atoms. Alternatively, alkenyl groups may have 2 to 12 carbon atoms, alternatively 2 to 10 carbon atoms, alternatively 2 to 6 carbon atoms, alternatively 2 to 4 carbon atoms, and alternatively 2 carbon atoms.

"Alkynyl" means an acyclic, branched, or unbranched unsaturated monovalent hydrocarbon group, where the monovalent hydrocarbon group has a triple bond. Alkynyl groups include ethynyl and propynyl. Alkynyl groups have at least 2 carbon atoms. Alternatively, alkynyl groups may have 2 to 12 carbon atoms, alternatively 2 to 10 carbon atoms, alternatively 2 to 6 carbon atoms, alternatively 2 to 4 carbon atoms, and alternatively 2 carbon atoms.

"Aryl" means a hydrocarbon group derived from an arene by removal of a hydrogen atom from a ring carbon atom. Aryl is exemplified by, but not limited to, Ph and naphthyl. Aryl groups have at least 5 carbon atoms. Monocyclic aryl groups may have 5 to 9 carbon atoms, alternatively 6 to 7 carbon atoms, and alternatively 6 carbon atoms. Polycyclic aryl groups may have 10 to 17 carbon atoms, alternatively 10 to 14 carbon atoms, and alternatively 12 to 14 carbon atoms.

"Carbocycle" and "carbocyclic" refer to a hydrocarbon ring. Carbocycles may be monocyclic or polycyclic, e.g., bicyclic or with more than two rings. Bicyclic carbocycles may be fused, bridged, or spiro polycyclic rings. Carbocycles have at least 3 carbon atoms. Monocyclic carbocycles may have 3 to 9 carbon atoms, alternatively 4 to 7 carbon atoms, and alternatively 5 to 6 carbon atoms. Polycyclic carbocycles may have 7 to 17 carbon atoms, alternatively 7 to 14 carbon atoms, and alternatively 9 to 10 carbon atoms. Carbocycles may be saturated (e.g., cyclopentane or cyclohexane), partially unsaturated (e.g., cyclopentene or cyclohexene), or fully unsaturated (e.g., cyclopentadiene or cycloheptatriene).

"Cycloalkyl" refers to a saturated hydrocarbon group including a carbocycle. Cycloalkyl groups are exemplified by cyclobutyl, cyclopentyl, cyclohexyl, and methylcyclohexyl. Cycloalkyl groups have at least 3 carbon atoms. Monocyclic cycloalkyl groups may have 3 to 9 carbon atoms, alternatively 4 to 7 carbon atoms, and alternatively 5 to 6 carbon atoms. Polycyclic cycloalkyl groups may have 7 to 17 carbon atoms, alternatively 7 to 14 carbon atoms, and alternatively 9 to 10 carbon atoms.

"Spinel" means a compound of empirical formula $MM'_2O_4$, where M and M' are cations, each of M and M' can be a divalent, a trivalent or a quadrivalent cation, and where the oxygen atoms have a cubic close-packed structure. The cubic close-packed structure can be seen in an XRD spectrum.

"Metallic" means that the metal has an oxidation number of zero.

"Purging" means introducing a gas stream into a container and removing a mixture of the gas stream and unwanted materials from the container.

"Treating" means introducing a gas stream into a container to pre-treat a component, e.g., before contacting the component with another component. Treating includes contacting the reactant to reduce or otherwise activate it before contacting it with the organohalide in step (2) of the method. Treating may further include contacting the spinel catalyst to reduce or otherwise activate it before contacting it with the ingredients comprising the $H_2$ and the silane in step (1) of the method.

"Residence time" means the time which a component takes to pass through a reactor system in a continuous process, or the time a component spends in the reactor in a batch process. For example, residence time in step (1) refers to the time during which one reactor volume of the spinel catalyst makes contact with the ingredient comprising the silane as the spinel catalyst passes through the reactor system in a continuous process or during which the spinel catalyst is placed within the reactor in a batch process. Alternatively, residence time may refer to the time for one reactor volume of reactive gases to pass through a reactor charged with the spinel catalyst in step (1). (E.g., residence time includes the time for one reactor volume of and the ingredient comprising the silane in step (1) to pass through a reactor charged with the spinel catalyst or the time for one reactor volume of organohalide to pass through a reactor charged with the reactant in step (2) of the method described herein.)

"Reactant" means a solid product that is formed in step (1) of the method described herein, and/or re-formed in step (3) of the method described herein.

"Spent reactant" refers to the reactant after it has been contacted with the organohalide. For example, spent reactant may be present after step (2) (or after step (4), when step (4) is present in the method). The spent reactant after step (2) (or step (4)) contains an amount of silicon that is less than the amount of silicon in the reactant before beginning step (2) (or after step (3) and before beginning step (4)). Spent reactant may, or may not, be exhausted, i.e., spent reactant may contain some silicon that may or may not be reactive with the organohalide.

In one embodiment, the method for preparing the reaction product comprising the halosilane comprises steps (1) and (2), where:

step (1) is contacting, at a temperature from 200° C. to 1400° C., a first ingredient comprising a silane of formula $H_aR_bSiX_{(4-a-b)}$, where subscript a is an integer from 0 to 4, subscript b is 0 or 1, a quantity (a+b)≤4, each R is independently a monovalent organic group, and each X is independently a halogen atom, with the proviso that when the quantity (a+b)<4, then the ingredients further comprise $H_2$; and a spinel catalyst comprising copper; thereby forming a reactant; and step (2) is contacting the reactant and a second ingredient comprising an organohalide at a temperature from 100° C. to 600° C.; thereby forming the reaction product and a spent reactant; and where the method optionally further comprises steps (3) and (4), where when steps (3) and (4) are present, steps (3) and (4) may be performed separately and consecutively after step (2), and where step (3) is contacting, at a temperature from 200° C. to 1400° C., the spent reactant with an additional first ingredient comprising an additional silane of formula $H_aR_b SiX_{(4-a-b)}$, where subscript a is an integer from 0 to 4, subscript b is 0 or 1, the quantity (a+b)≤4, each R is independently a monovalent organic group, and each X is independently a halogen atom, with the proviso that when the quantity (a+b)<4, then the additional ingredient further comprises $H_2$; thereby re-forming the reactant, and step (4) is contacting the reactant re-formed in step (3) with an additional second ingredient comprising an organohalide at a temperature from 100° C. to 600° C.; and where the method optionally further comprises step (5), where step (5) is repeating steps (3) and (4) at least one time; and where the method optionally further comprises step (6) after any one or more of steps (2) to (5), where step (6) is recovering the halosilane.

Steps (1) and (2) may be performed separately and consecutively. Steps (3) and (4), when present, may also be performed separately and consecutively. "Separate" and "separately" mean that step (1) and step (2) do not overlap or coincide. "Consecutive" and "consecutively" mean that step (2) is performed after step (1) in the method; however, additional steps may be performed between step (1) and (2), as described below. "Separate" and "separately" refer to either spatially or temporally or both. "Consecutive" and "consecutively" refers to temporally (and furthermore occurring in a defined order). Alternatively, steps (1) and (2)

are performed separately and consecutively. Alternatively, steps (3) and (4) are present and are performed separately and consecutively.

The silane used in step (1) has formula $H_aR_bSiX_{(4-a-b)}$, where subscript a is an integer from 0 to 4, subscript b is 0 to 2, and a quantity $(a+b) \leq 4$. Alternatively, subscript a may be 0 or 1, subscript b may be 0 or 1, and $0 \leq (a+b) \leq 1$. Each R is independently a monovalent organic group, and each X is independently a halogen atom. Alternatively, in the formula $H_aR_bSiX_{(4-a-b)}$, each X may be independently selected from Br, Cl, and I; alternatively Br and Cl; alternatively Cl and I; and alternatively each X may be Cl. Each R may be a hydrocarbyl group. Each R may be independently selected from alkyl, alkenyl, alkynyl, aryl, aralkyl, and carbocyclic as defined above. Alternatively, each R may be a hydrocarbyl group independently selected from alkyl, aryl, and carbocyclic. Alternatively, each R may be alkyl, such as Me, Et, Pr, or Bu; alternatively Me. The silane may comprise a tetrahalosilane ($SiX_4$), a trihalosilane ($HSiX_3$), a dihalosilane ($H_2SiX_2$), a monohalosilane ($H_3SiX$), silane ($SiH_4$), or a combination thereof. Alternatively, the silane may comprise a tetrahalosilane, a trihalosilane, or a combination thereof. Alternatively, the silane may be a tetrahalosilane of formula $SiX_4$, (i.e., where a=0 and b=0 in the formula above) where each X is as described above. Examples of the tetrahalosilane include, but are not limited to, silicon tetrachloride, silicon tetrabromide, silicon tetraiodide, and silicon tetrafluoride. Alternatively, the silane may be a trihalosilane such as $HSiX_3$, (where a=1 and b=0 in the formula $H_aR_bSiX_{(4-a-b)}$) and/or $RSiX_3$, (where a=0 and b=1 in the formula $H_aR_bSiX_{(4-a-b)}$), where R and X are as described above. Examples of trihalosilanes include trichlorosilane ($HSiCl_3$), tribromosilane, methyltrichlorosilane ($CH_3SiCl_3$), methyltribromosilane, ethyltrichlorosilane, ethyltribromosilane, and a combination thereof. Alternatively, when the silane used comprises $SiH_4$, then in step (1), $H_2$ may be omitted; when the quantity $(a+b)<4$, then in step (1) the ingredients further comprise $H_2$. The silane used in step (1) is distinct from the halosilane in the reaction product.

The spinel catalyst used in step (1) comprises copper and a spinel. In one embodiment, the copper may be part of the spinel, e.g., in the spinel of empirical formula $MM'_2O_4$, M may be Cu and the spinel catalyst may have empirical formula $CuM'_2O_4$, where M' is Al, Cr, Fe, Mg, or Ni; alternatively Al, Fe, or Ni; alternatively Al or Fe; and alternatively Al. In this embodiment, the spinel catalyst may comprise one or more of $CuAl_2O_4$ or $CuFe_2O_4$. Alternatively, excess support, such as alumina may be present, for example, when the spinel catalyst is one of the spinel catalysts prepared as described below in the examples, e.g., 20% $CuAl_2O_4$, 30% $CuAl_2O_4$, 43.8% $CuAl_2O_4$, or 13% $CuAl_2O_4$.

Alternatively, the spinel catalyst may further comprise one or more additional metals promoted with the spinel such as Au, or Mg, e.g., in metallic form or a metal compound (such as $AuCl_3$ or $MgCl_2$) promoted with the spinel (such as Au and/or Mg promoted with a spinel of empirical formula $CuAl_2O_4$). For example, the spinel catalyst may be Au—Mg—$CuAl_2O_4$, prepared as described below in the examples, sample 2(c).

Alternatively, the spinel catalyst may comprise copper supported on a spinel, e.g., in the form of a copper compound (such as copper oxide) supported on the spinel. For example, the spinel catalyst may comprise one or more of, $CuO/NiAl_2O_4$, $CuO/MgAl_2O_4$, $CuO/CuAl_2O_4$ or $2CuO.Cr_2O_3$. Alternatively, a portion of the copper may form part of the spinel and another portion of the copper in the spinel catalyst may be supported on the spinel. For example, the catalyst may comprise a copper compound supported on a spinel which contains copper as part of the spinel. In this embodiment, the spinel catalyst may comprise one or more of $CuO/CuAl_2O_4$, 30% Cu/10% $CuAl_2O_4$, or 30% Cu/20% $CuAl_2O_4$.

The spinel catalyst may be prepared by a method comprising:
i) combining a support and a precursor comprising copper, thereby forming a combination support; and
ii) calcining the combination to form the spinel catalyst.

Step i) may be performed by any convenient means, such as incipient wetness impregnation or co-precipitation or sol-gel or physical blending of metal oxides. In one embodiment, step i) is performed by impregnating the support with the precursor. The term "impregnating" means permeating with a wetted, melted, or molten substance substantially throughout a support (e.g., via an incipient wetness technique), preferably to a point where essentially all of a liquid phase substance is adsorbed, producing a liquid-saturated but unagglomerated solid. An illustrative example of the impregnating technique may be found in Example 1 of WO 2011/106194. Alternatively, impregnating in step i) may be performed by a depositing-adsorbing technique, such as that found in Example 3 of WO 2011/106194. The precursor may comprise, for example, an aqueous solution of $Cu(NO_3)_2$, $CuCl_2$, or Cu-acetylacetonate. The aqueous solution may optionally further comprise an acid, such as HCl. The support may be, for example, alumina, $Fe_2O_3$, $Cr_2O_3$, $SiO_2$, MgO, $La_2O_3$ or $ZrO_2$. Alternatively, the support may be alumina.

Step ii) is performed by calcining. Calcining may be performed by heating the combination produced in step i) in an atmosphere, at a temperature, and for a time sufficient to form a spinel. Calcining is performed at a temperature greater than 700° C.; alternatively calcining is performed a temperature of at least 800° C. For example, calcining may be performed by heating at a temperature of 800° C. to 1200° C., alternatively 900° C. to 1000° C. Calcining is performed in an atmosphere containing sufficient oxygen for the spinel to form. For example, calcining may be performed in air. The exact time for calcining depends on various factors including the temperature and reactants selected, however, calcining may be performed for at least 1 hour; alternatively 3 to 12 hours, alternatively 6 to 8 hours.

The method for preparing the spinel catalyst may optionally further comprise one or more additional steps. The method may optionally further comprise drying the support before step i) and/or drying the combination after step i) and before step ii). Drying may be performed by heating for a time sufficient to remove water, e.g., at a temperature of 100° C. to 120° C. The method may optionally further comprise heating the combination after step i) and before step ii). Heating may be performed at a temperature less than that required for calcining to form the spinel catalyst. For example, the combination may be heated at 300° C. to 700° C. for 1 to 8 hours before calcining. The method may optionally further comprise repeating steps i) and ii) to add additional copper to the spinel. The Cu precursor used may be the same Cu precursor, or a different Cu precursor, than that used in steps i) and ii).

Alternatively, the method may optionally further comprise steps a) and b), which may be performed before step i), and/or after step ii), and where step a) is combining a support and an additional metal precursor, thereby forming a further combination; step b) is calcining the further combination to form the spinel catalyst; and the metal in the additional metal precursor is a metal other than copper. The metal precursor may be in a form as described above for the precursor described above for step 1), e.g., the metal precursor may be in an aqueous solution, optionally containing an acid. The metal precursor may comprise one or more of $Ni(NO_3)_2$, $AuCl_3$, or $MgCl_2$. Alternatively, the additional metal precursor may be added with the Cu precursor during step i).

Alternatively, the spinel catalyst may be prepared by a method comprising calcining a commercially available copper containing oxide to form a spinel. For example, step i) of the method may be eliminated when a compound such as CuO on $Al_2O_3$, which is available from Sigma-Aldrich, Inc. of St. Louis, Mo., USA, is used in step ii) of the method described above to prepare the spinel catalyst. Alternatively, the spinel catalyst may be a commercially available spinel compound, such as a copper iron oxide ($CuFe_2O_4$), or a copper chromate $2CuO.Cr_2O_3$, which are available from Sigma-Aldrich, Inc. of St. Louis, Mo., USA.

Alternatively, the spinel catalyst may be prepared by a method comprising:
i) combining copper oxide and a second metal oxide, where the second metal oxide differs from copper oxide; and
ii) calcining the combination to form the spinel catalyst.

This method may be used to prepare the spinel catalyst in situ, i.e., in the same reactor that is used to perform step (1). In step i) of the in situ method for preparing the spinel catalyst, copper oxide (CuO) is combined with a second metal oxide. The copper oxide and second metal oxide may be physically blended by mixing by any convenient means, such as combining them in a fluidized bed reactor and fluidizing them, or by mixing before placing them in the reactor. The second metal oxide may be selected from the group consisting of $Al_2O_3$, $Cr_2O_3$, and $Fe_2O_3$. Alternatively, the second metal oxide may be $Al_2O_3$.

Step ii) is performed by calcining. Calcining may be performed by heating the combination produced in step i) in an atmosphere, at a temperature, and for a time sufficient to form a spinel. Calcining is performed at a temperature greater than 700° C.; alternatively calcining is performed a temperature of at least 800° C. For example, calcining may be performed by heating at a temperature of 750° C. to 1200° C., alternatively 750° C. to 1000° C., and alternatively 800° C. to 950° C. Calcining is performed in an atmosphere containing sufficient oxygen for the spinel to form. For example, calcining may be performed in air and/or an inert gas such as nitrogen or argon. The exact time for calcining depends on various factors including the temperature and metal oxides selected, however, calcining may be performed for at least 1 hour; alternatively 1 to 15 hours, alternatively 3 to 12 hours, and alternatively 6 to 8 hours.

The reactor in which step (1) is performed may be any reactor suitable for the combining of gases and solids. For example, the reactor configuration can be a batch vessel, packed bed, stirred bed, vibrating bed, moving bed, re-circulating beds, or a fluidized bed. When using re-circulating beds, the spinel catalyst can be circulated from a bed for conducting step (1) to a bed for conducting step (2). To facilitate reaction, the reactor should have means to control the temperature of the reaction zone, e.g., the portion of the reactor in which the silane (and optionally the $H_2$) contact the spinel catalyst in step (1) and/or the portion of the reactor in which the organohalide contacts the reactant in step (2).

The temperature at which the ingredient comprising the silane is contacted with the spinel catalyst in step (1) may be from 200° C. to 1400° C.; alternatively 500° C. to 1400° C.; alternatively 600° C. to 1200° C.; and alternatively 650° C. to 1100° C.

The pressure at which the ingredient comprising the silane is contacted with the spinel catalyst in step (1) can be sub-atmospheric, atmospheric, or super-atmospheric. For example, the pressure may range from 10 kilopascals absolute (kPa) to 2100 kPa; alternatively 101 kPa to 2101 kPa; alternatively 101 kPa to 1101 kPa; and alternatively 101 kPa to 900 kPa; and alternatively 201 kPa to 901 kPa.

The mole ratio of $H_2$ to silane contacted with the spinel catalyst in step (1) may range from 10,000:1 to 0.01:1, alternatively 100:1 to 1:1, alternatively 20:1 to 5:1, alternatively 20:1 to 4:1, alternatively 20:1 to 2:1, alternatively 20:1 to 1:1, and alternatively 4:1 to 1:1.

The residence time for the ingredient comprising the silane is sufficient for the ingredient comprising the silane to contact the spinel catalyst and form the reactant in step (1). For example, a sufficient residence time for the ingredient comprising the silane may be at least 0.01 s, alternatively at least 0.1 s, alternatively 0.1 s to 10 min, alternatively 0.1 s to 1 min, alternatively 0.5 s to 10 s, alternatively 1 min to 3 min, and alternatively 5 s to 10 s. Alternatively, the residence time for the spinel catalyst to be in contact with the ingredient comprising the silane in step (1) is typically at least 0.1 min; alternatively at least 0.5 minutes; alternatively 0.1 min to 120 min; alternatively 0.5 min to 9 min; alternatively 0.5 min to 6 min. The desired residence time may be achieved by adjusting the flow rate of the $H_2$ and the silane, or by adjusting the total reactor volume, or by any combination thereof. The desired residence time of the reactant may be achieved by adjusting the flow rate of the reactant, or by adjusting the total reactor volume, or a combination thereof.

In step (1), when $H_2$ is present, the $H_2$ and the silane may be fed to the reactor simultaneously; however, other methods of combining, such as by separate pulses, are also envisioned. The $H_2$ and the silane may be mixed together before feeding to the reactor; alternatively, the $H_2$ and the silane may be fed into the reactor as separate streams.

In step (1), the spinel catalyst is in a sufficient amount. A sufficient amount of spinel catalyst is enough spinel catalyst to form the reactant, described below, when the ingredient comprising the silane is contacted with the spinel catalyst. For example, a sufficient amount of spinel catalyst may be at least 0.01 mg catalyst/$cm^3$ of reactor volume; alternatively at least 0.5 mg catalyst/$cm^3$ of reactor volume, and alternatively 1 mg catalyst/$cm^3$ of reactor volume to maximum bulk density of the spinel catalyst based on the reactor volume, alternatively 1 mg to 5,000 mg catalyst/$cm^3$ of reactor volume, alternatively 1 mg to 1,000 mg catalyst/$cm^3$ of reactor volume, and alternatively 1 mg to 900 mg catalyst/$cm^3$ of reactor volume.

Step (1) is conducted for the residence time of the spinel catalyst, where residence time is as defined above. There is no upper limit on the time for which step (1) is conducted. For example, step (1) is usually conducted for at least 0.1 s, alternatively from 1 s to 5 hr, alternatively from 1 min to 1 hr.

The product of step (1) is the reactant. The reactant comprises an amount of silicon of at least 0.1%, alternatively 0.1% to 90%, alternatively 1% to 50%, alternatively 1% to 35%, based on the total weight of reactant. The percentage of silicon in the reactant can be determined using standard analytical tests. For example, the percentage of Si may be determined using ICP-AES and ICP-MS.

Step (2) of the method is contacting the reactant with the organohalide at a temperature from 100° C. to 600° C.;

thereby forming the reaction product and the spent reactant. The organohalide may have formula RX, where R is a monovalent organic group and X is a halogen atom. The halogen atom selected for X in the organohalide may be the same as the halogen atom selected for X in the silane used in step (1). Alternatively, the halogen atom selected for X in the organohalide may differ from the halogen atom selected for X in the silane used in step (1). The group selected for R in the organohalide may be the same as the group selected for R for the silane described above in step (1) (when subscript b>0 in the formula $H_aR_bSiX_{(4-a-b)}$). Alternatively, the group selected for R in the organohalide may differ from the group selected for R in the silane described above for step (1). Alternatively, R may be selected from alkyl, alkenyl, alkynyl, aryl, aralkyl, and carbocyclic as defined above. Alternatively, R may be a hydrocarbyl group selected from alkyl, aryl, and carbocyclic. Alternatively, each R may be alkyl, such as Me, Et, Pr, or Bu; alternatively Me. Alkyl groups containing at least three carbon atoms can have a branched or unbranched structure. Alternatively, each X may be independently selected from Br, Cl, and I; alternatively Br and Cl; alternatively Cl and I; and alternatively each X may be Cl. Examples of the organohalide include, but are not limited to, methyl chloride, methyl bromide, methyl iodide, ethyl chloride, ethyl bromide, ethyl iodide, cyclobutyl chloride, cyclobutyl bromide, cyclohexyl chloride, and cyclohexyl bromide.

The reactors suitable for use in step (2) are as described for step (1). The same reactor may be used for step (1) as used in step (2). Alternatively, separate reactors may be used for steps (1) and (2). When separate reactors are used, the type of reactor in each step may be the same or different. In step (2), the organohalide may be contacted with the reactant by feeding the organohalide into a reactor containing the reactant produced in step (1).

The residence time of the organohalide is sufficient for the organohalide to react with the reactant to form the reaction product comprising the halosilane in step (2). For example, a sufficient residence time of the organohalide may be at least 0.01 s, alternatively at least 0.1 s, alternatively 0.5 s to 10 min, alternatively 1 s to 1 min, alternatively 1 s to 10 s. The desired residence time can be achieved by adjusting the flow rate of the organohalide, or the total reactor volume, or a combination thereof.

The residence time for the reactant to be in contact with the organohalide in step (2) is typically at least 1 minute; alternatively at least 5 minutes; alternatively 1 min to 120 min; alternatively 5 min to 90 min; alternatively 5 min to 60 min. Alternatively, there is no upper limit on the residence time for which step (2) is conducted. The desired residence time of the reactant in step (2) may be achieved by adjusting the flow rate of the reactant, or by adjusting the total reactor volume, or a combination thereof.

The temperature at which organohalide is contacted with the reactant in step (2) may be from 100° C. to 600° C., alternatively 200° C. to 500° C., alternatively 250° C. to 375° C., and alternatively at least 220° C.

Step (2) is typically conducted until the amount of silicon in the reactant falls below a predetermined limit, e.g., until the reactant is spent. For example, step (2) may be conducted until the amount of silicon in the reactant is below 90%, alternatively 1% to 90%, alternatively 1% to 40%, of its initial weight percent. The initial weight percent of silicon in the reactant is the weight percent of silicon in the reactant before the reactant is contacted with the organohalide in step (2). The amount of silicon in the reactant can be monitored by correlating production of the reaction product of step (2) with the weight percent of silicon in the reactant and then monitoring the reactor effluent or may be determined as described above. Alternatively, step (2) is conducted until at least 1% of the silicon contributed in step (1) is reacted; alternatively, step (2) is conducted until 1% to 40% of the silicon contributed in step (1) is reacted; alternatively, step (2) is conducted until at least 90% of the silicon contributed in step (1) is reacted; alternatively step (2) is conducted until greater than 95% of the silicon contributed in step (1) is reacted, alternatively step (2) is conducted until greater than 99% of the silicon contributed in step (1) is reacted, and alternatively step (2) is conducted until 99.9% of the silicon contributed in step (1) is reacted.

The pressure at which the organohalide is contacted with the reactant in step (2) can be sub-atmospheric, atmospheric, or super-atmospheric. For example, the pressure may range from 10 kilopascals absolute (kPa) to 2100 kPa; alternatively 101 kPa to 2101 kPa; alternatively 101 kPa to 1101 kPa; and alternatively 101 kPa to 900 kPa; and alternatively 201 kPa to 901 kPa.

The reactant is present in a sufficient amount. A sufficient amount of reactant is enough reactant to form the halosilane, described herein, when the reactant is contacted with the organohalide. For example, a sufficient amount of reactant may be at least 0.01 mg catalyst/cm$^3$ of reactor volume; alternatively at least 0.5 mg catalyst/cm$^3$ of reactor volume; alternatively 0.01 mg catalyst/cm$^3$ of reactor volume to maximum bulk density of the reactant in the reactor volume, alternatively 1 mg to 5,000 mg catalyst/cm$^3$ of reactor volume, alternatively 1 mg to 1,000 mg catalyst/cm$^3$ of reactor volume, and alternatively 1 mg to 900 mg catalyst/cm$^3$ of reactor volume.

The resulting reaction product of the method described above comprises the halosilane. The halosilane may have general formula $R_{(4-c)}SiX_c$, where each X is independently a halogen atom, and each R is independently a monovalent organic group, as described above; and subscript c is 1, 2, 3, or 4. Alternatively, the halosilane may be a diorganodihalosilane of formula $R_2SiX_2$, where each X is independently a halogen atom, and each R is independently a monovalent organic group, as described above. Alternatively, the halosilane may be a mixture of two or more organohalosilanes, e.g., a diorganodihalosilane and an organotrihalosilane or two or more different diorganodihalosilanes.

The method described herein may optionally further comprise purging and/or treating. Purging and/or treating may be performed at various times during the method. For example, the method described herein may optionally further comprise one or more of the following purging and/or treating steps:

purging and/or treating the spinel catalyst, before contacting the spinel catalyst with the ingredient comprising the silane in step (1); and/or purging and/or treating the reactant, before contacting the reactant with the organohalide in step (2); and/or purging and/or treating, the spent reactant before contacting the spent reactant with the additional ingredient in step (3); and/or purging and/or treating the reactant re-formed in step (3), before the contacting the reactant re-formed in step (3) with the (additional) organohalide in step (4); and/or purging and/or treating the additional spent reactant. The purging step comprises introducing a gas stream into the reactor containing the spinel catalyst, the reactant, and/or the spent reactant to remove unwanted materials in step (2), and when present step (4), may include, for example, $H_2$, $O_2$, $H_2O$ and HX, where X is a halogen atom as defined above. Purging may be accomplished with an inert gas, such as argon or nitrogen, or with a reactive gas, such as the organohalide; alternatively purging may be performed with an inert gas. The treating step may comprise introducing a gas stream into the reactor containing the spinel catalyst to pre-treat the spinel catalyst before contacting it with the ingredient comprising the silane. Alternatively, the treating step may comprise introducing a gas stream into the reactor containing the reactant to activate and/or reduce it before contacting the reactant with the organohalide. Treating may be accomplished with a gas, such as $H_2$ or the organohalide; alternatively $H_2$. Purging and/or treating may be performed at ambient or elevated temperature, e.g., at least 25° C., alternatively at least 300° C., alternatively 25° C. to 500° C., and alternatively 300° C. to 500° C.

Alternatively, treating may be performed heating, under $H_2$, the spinel catalyst produced in step ii) of the method for preparing the spinel catalyst described above. Without wishing to be bound by theory, it is thought that this may form metallic copper supported on a spinel, when the spinel catalyst described above has a copper compound supported on the spinel.

In step (2) of the method the reactant and the organohalide may be contacted in the absence of $H_2$, in the absence of the silane, or in the absence of both $H_2$ and the silane.

The method may optionally further comprise steps (3) and (4) after step (2). Steps (3) and (4) may be performed separately and consecutively. The purpose of steps (3) and (4) is to recycle spent reactant by repeating steps (1) and (2), e.g., using spent reactant in place of the spinel catalyst used in step (1) of the method. The spent reactant after step (2) contains an amount of silicon less than the amount of silicon in the reactant before beginning step (2). The spent reactant left after step (4) contains an amount of silicon less than the amount of silicon in the reactant re-formed in step (3). The amount of silicon contributed to the reactant in a step (3) less the amount of said silicon consumed in the next step (4) is referred to as the Si difference. For any given cycle comprising a step (3) and a step (4), the Si difference may be greater than 90% of the amount of silicon deposited in the step (3) for that cycle. Alternatively, the Si difference may be greater than 95%. Alternatively, the Si difference may be greater than 99%. Alternatively, the Si difference may be greater than 99%. Alternatively, the Si difference may be 90% to 99.9%.

Step (3) comprises contacting the spent reactant with an additional ingredient comprising an additional silane, under conditions as described above for step (1), at a temperature from 200° C. to 1400° C. to re-form the reactant comprising at least 0.1% of Si. The additional silane used in step (3) may be more of the same silane used above in step (1). Alternatively, the additional silane used in step (3) may be a silane of formula $H_aR_bSiX_{(4-a-b)}$, where at least one instance of R, X, subscript a, or subscript b is different than that used in the silane in step (1). $H_2$ may be used in step (3) as described above for step (1). Step (4) comprises contacting the reactant re-formed in step (3) with an additional second ingredient comprising (additional) organohalide (under conditions as described for step (2), above) at a temperature from 100° C. to 600° C. to form the reaction product comprising the halosilane. The additional second ingredient may be the same as, or different from, the second ingredient comprising the organohalide selected in step (2). Alternatively, the additional second ingredient used in step (4) may be the same as the second ingredient used in step (2).

Without wishing to be bound by theory, it is thought that the method described herein allows for maximizing the number of cycles for repeating steps (3) and (4). The method may optionally further comprise step (5), which is repeating steps (3) and (4) at least 1 time, alternatively from 1 to $10^5$ times, alternatively from 1 to 1,000 times, alternatively from 1 to 100 times, and alternatively from 1 to 10 times.

If the organohalide (or the silane) are liquids at or below standard temperature and pressure, the method may further comprise pre-heating and gasifying the organohalide (and/or the silane) by known methods before contacting the silane with the spinel catalyst in step (1), and/or the spent reactant step (3), and/or before contacting the organohalide with the reactant in step (2) and/or step (4). Alternatively, the method may further comprise bubbling the $H_2$ through liquid silane to vaporize the silane before contacting with the spinel catalyst in step (1), and/or the spent reactant in step (3).

If the silane is a solid at or below standard temperature and pressure, the method may further comprise pre-heating above the melting point and liquefying or vaporizing the silane before bringing it in contact with the spinel catalyst in step (1) and/or the spent reactant in step (3). If the organohalide is a solid at or below standard temperature and pressure, the method may further comprise pre-heating above the melting point and liquefying or vaporizing the organohalide before bringing it in contact with reactant in step (2) and/or step (4).

The method may optionally further comprise step (5). Step (5) comprises recovering the reaction product produced (i.e., product of step (2) and/or step (4)). The reaction product comprises the halosilane described above. The halosilane may be recovered from the reaction product by, for example, removing gaseous product from the reactor followed by isolation by distillation. The halosilane may have general formula $R_{(4-c)}SiX_c$, where each X is independently a halogen atom, and each R is independently a monovalent organic group, as described above; and subscript c is 0, 1, 2, or 3. Alternatively, the halosilane may have formula $R_2SiX_2$, where each R and X are as described above. Exemplary halosilanes that may be produced by the method include organotrihalosilanes and/or diorganodihalosilanes. Organotrihalosilanes are exemplified by methyltrichlorosilane, methyltribromosilane, and ethyltrichlorosilane. Examples of diorganodihalosilanes prepared according to the present process include, but are not limited to, dimethyldichlorosilane (i.e., $(CH_3)_2SiCl_2$), dimethyldibromosilane, diethyldichlorosilane, and diethyldibromosilane. Examples of other organohalosilanes that may be produced in addition to the diorganodihalosilane include, but are not limited to, methyltrichlorosilane (i.e., $CH_3SiCl_3$), and methyltribromosilane (i.e., $CH_3SiBr_3$).

A hydrogen halide may be present in the reaction product produced according the present method. The hydrogen halide has formula HX, where X is as defined above. The hydrogen halide may be separated from the halosilane via condensation, distillation, or other means and collected or fed to other chemical processes.

The method described herein produces halosilanes, particularly organohalosilanes such as diorganodihalosilanes. The organohalosilanes may be used as reactants in hydrolysis processes to produce polyorganosiloxanes. Diorganodihalosilanes, such as dimethyldichlorosilane, can be used as reactants in processes for producing polydiorganosiloxanes. Organotrihalosilanes may be used as reactants in processes for producing polyorganosiloxanes, such as resins. The polyorganosiloxanes thus produced find use in many industries and applications.

The method described herein may offer the advantage of not producing large amounts of metal halide byproducts requiring costly disposal. Still further, the method may have good selectivity to produce diorganodihalosilanes, as compared to other halosilanes. Finally, the reactant may be re-formed and reused in the method, and the re-forming and reuse may provide increasing diorganodihalosilane production and/or selectivity.

EXAMPLES

These examples are intended to illustrate some embodiments of the invention and should not be interpreted as limiting the scope of the invention set forth in the claims. In the tables below, 'nd' means not done or not determined.

The reaction apparatus used in these examples comprised a 4.8 mm inner diameter quartz glass tube in a flow reactor. The reactor tube was heated using a Lindberg/Blue Minimite 2.54 cm tube furnace. Brooks instrument 5850E mass flow controllers were used to control gas flow rates. A stainless steel $SiCl_4$ bubbler was used to introduce $SiCl_4$ into the $H_2$ gas stream. The amount of $SiCl_4$ in the $H_2$ gas stream was adjusted by changing the temperature of the $SiCl_4$ in the bubbler according to calculations using well-known thermodynamic principles. For reactions run at pressures above atmospheric pressure, a back pressure regulator (GO type Hastelloy® rated for 0-500 psig) was introduced at the back end of the reactor.

The effluent of the reactor containing the reaction product was passed through an actuated 6-way valve (Vici) with constant 1 ml injection loop before being discarded. Samples were taken from the reaction effluent stream by actuating the injection valve and the 1 ml sample passed directly into the injection port of a 6890A Agilent GC for analysis with a split ratio at the injection port of 75:1. The GC contained a single column suitable for analysis of chlorosilanes, which was split at the outlet. Both paths went to thermal conductivity detectors (TCD) for quantization of the reaction products.

In comparative example 1, 7.0 grams of alumina (DAVI-CAT AL2720) was impregnated with 10.9805 grams of $Cu(NO_3)_2.2.5H_2O$ (ALDRICH 12837) taken in 30 ml de-ionized water. The resultant mixture was placed on a hot plate to remove excess solvent. The resulting material was further dried in hot air oven at 200° C. for 12 hours. The resulting material was an alumina supported copper catalyst.

The activity of this alumina supported copper catalyst was evaluated in a fixed bed reactor in gas phase. The alumina supported copper catalyst (0.5 g) was placed in the fixed bed reactor and reduced by feeding $H_2$ at 500° C. and 100 sccm through the reactor for 3-4 hours. After this, a mixture of $H_2$ and $SiCl_4$ was fed through the reactor for 30 min at 750° C. by bubbling $H_2$ through a stainless steel $SiCl_4$ bubbler. The total flow of $H_2$ and $SiCl_4$ was 150 sccm, and the mole ratio of $H_2$ to $SiCl_4$ was 4:1. The $SiCl_4$ flow was controlled by $H_2$ flow by keeping the bubbler temperature at 14.6° C. The gas and vapor leaving the bubbler was fed into the reactor containing the alumina supported copper catalyst to form a Si-containing copper catalyst comprising 33% Si. After 30 minutes, the $SiCl_4$ flow was ceased and a $H_2$ flow of 100 sccm was maintained while cooling to 300° C. over a period of 1 hour.

When the reactor reached 300° C., $H_2$ was purged from the reactor with an argon flow of 50 sccm for 30 min. After 30 min, the argon flow was ceased, and $CH_3Cl$ was fed through the reactor at a flow rate of 5 sccm, a temperature of 300° C. and atmospheric pressure for 60 min. The reactor effluent was periodically sampled and analyzed by GC to determine the weight percent of $(CH_3)_2SiCl_2$ and other chlorosilanes based on the total mass leaving the reactor.

Next, the $CH_3Cl$ feed was ceased, and the spent Si-containing copper catalyst was treated with $H_2$ at 500° C. for 30-60 min and contacted again with $H_2/SiCl_4$ for 30 min at 750° C. to re-form the Si-containing copper catalyst. The combined flow rate of $H_2$ and $SiCl_4$ was 150 sccm, and the mole ratio of $H_2$ to $SiCl_4$ was 4:1. After the Si-containing copper catalyst was re-formed, the reactor was again purged with argon, and $CH_3Cl$ was contacted with the re-formed Si-contained copper catalyst as described above. This cycle was repeated 10 times. The results are shown in Table C1.

TABLE C1

| Cycle (#) | Si deposited (g) | Si removed (g) | Si conversion (%) | $Me_2SiCl_2$ selectivity (%) | $MeSiCl_3$ selectivity (%) | Others selectivity (%) |
|---|---|---|---|---|---|---|
| 1 | 0.176 | 0.030 | 17.3 | 81 | 15 | 4 |
| 3 | 0.162 | 0.019 | 12 | 65 | 24 | 11 |
| 4 | 0.160 | 0.014 | 9 | 69 | 26 | 6 |
| 5 | 0.160 | 0.017 | 11 | 69 | 26 | 5 |
| 6 | 0.160 | 0.012 | 7 | 68 | 24 | 9 |
| 7 | 0.159 | 0.017 | 11 | 75 | 19 | 6 |
| 8 | 0.160 | 0.014 | 9 | 72 | 21 | 7 |
| 9 | 0.162 | 0.021 | 13 | 77 | 17 | 6 |
| 10 | 0.159 | 0.022 | 14 | 77 | 17 | 6 |
| 11 | 0.160 | 0.022 | 14 | 78 | 15 | 7 |

In comparative example 2, an alumina supported copper catalyst with a composition of 30% $Cu/Al_2O_3$ was synthesized using multiple impregnations of $Cu(NO_3)_2$ on 70 micron size alumina (Sud Chemie T2610) and heating in air at 700° C. The activity of this alumina supported copper catalyst was evaluated in a fixed bed reactor in gas phase. This catalyst was analyzed by XRD, which showed that the alumina supported copper catalyst was not a spinel catalyst. Without wishing to be bound by theory, it is thought that the minimum temperature for calcining must be greater than 700° C. to form a spinel catalyst from the reactants used in this example according to the method of this invention.

This alumina supported copper catalyst (1.5 g) was placed in a fixed bed reactor. The alumina supported copper catalyst was reduced under 100 sccm of $H_2$ at 500° C. for 3-4 hours. Next, a gaseous mixture of $H_2$ and $SiCl_4$ was fed to the reactor for 30 min at 750° C. by bubbling $H_2$ through a stainless steel $SiCl_4$ bubbler. The total flow of $H_2$ and $SiCl_4$ was 150 sccm with the mole ratio of $H_2$ to $SiCl_4$=4:1. The $SiCl_4$ flow was controlled by $H_2$ flow by keeping the bubbler temperature at 14.6° C. The gas and vapor leaving the bubbler was fed into the reactor containing the alumina supported copper catalyst to form a Si-containing copper catalyst comprising about 15% Si. After 30 minutes, the $SiCl_4$ flow was ceased, and a $H_2$ flow of 100 sccm was maintained while cooling to 300° C. over a period of 1 hour.

When the reactor reached 300° C., $H_2$ was purged from the reactor with an argon flow of 50 sccm for 30 min. After 30 min, the argon flow was ceased, and $CH_3Cl$ was fed through the reactor at a flow rate of 5 sccm, at a temperature of 300° C. and atmospheric pressure for 60 min. The reactor effluent was periodically sampled and analyzed by GC to determine the weight percent of $(CH_3)_2SiCl_2$ and other chlorosilanes based on the total mass of the reaction product leaving the reactor.

Next, the $CH_3Cl$ feed was ceased, and the spent Si-containing copper catalyst was treated with $H_2$ at 500° C. for 30-60 min and contacted again with $H_2/SiCl_4$ for 30 min at 750° C. to re-form the Si containing copper catalyst. The combined flow rate of $H_2$ and $SiCl_4$ was 150 sccm, and the mole ratio of $H_2$ to $SiCl_4$ was 4:1. After the Si-containing copper catalyst was re-formed, the reactor was purged with argon, and $CH_3Cl$ was contacted with the re-formed Si-contained copper catalyst as described above. This cycle was repeated 13 times. The results are shown in Table C2.

TABLE C2

| Cycle (#) | Si deposited (g) | Si removed (g) | Si conversion (%) | $Me_2SiCl_2$ selectivity (%) | $MeSiCl_3$ selectivity (%) | Others selectivity (%) |
|---|---|---|---|---|---|---|
| 1 | 0.283 | 0.065 | 23.1 | 76 | 17 | 7 |
| 2 | 0.198 | 0.051 | 25.8 | 74 | 18 | 9 |
| 3 | 0.217 | 0.032 | 14.8 | 61 | 20 | 19 |
| 4 | 0.199 | 0.030 | 15.3 | 68 | 18 | 13 |
| 5 | 0.197 | 0.039 | 19.8 | 70 | 19 | 11 |
| 6 | 0.197 | 0.049 | 25.2 | 66 | 16 | 18 |
| 7 | 0.200 | 0.054 | 26.8 | 69 | 19 | 12 |
| 8 | N/A | N/A | N/A | N/A | N/A | N/A |
| 9 | 0.216 | 0.050 | 23.0 | 76 | 14 | 10 |
| 10 | 0.216 | 0.041 | 19.2 | 68 | 20 | 12 |
| 11 | 0.271 | 0.064 | 23.5 | 71 | 15 | 13 |
| 12 | 0.207 | 0.055 | 26.4 | 75 | 17 | 9 |
| 13 | 0.265 | 0.045 | 16.9 | 66 | 19 | 15 |
| 14 | 0.193 | N/A | N/A | N/A | N/A | N/A |

Comparative example 1 shows that the activity of a supported copper catalyst $Cu/Al_2O_3$ catalyst, which is not a spinel catalyst, is low compared to $CuAl_2O_4$ spinel catalyst (where Cu loading is 35%, as 43.8% CuO), as shown in sample 2(e), below. Comparative examples 1 and 2 also showed formation of $AlCl_3$ after repeated cycles. No $AlCl_3$ was formed using the spinel catalysts in the examples below. Without wishing to be bound by theory, it is thought this is due to Cu—Al interaction in the spinel catalyst that is formed at high calcination temperature (e.g., ≥800° C.). Without wishing to be bound by theory, it is thought that a benefit of using a spinel catalyst is preventing $AlCl_3$ formation during step (1) of the method described herein, which enhances the catalyst life and process efficiency.

In example 1, methylchlorosilanes were produced over metal aluminate spinel supported copper catalysts. To prepare sample 1(a), 12.6 grams of alumina (DAVICAT AL2720) were dried by heating at 120° C. and impregnated with 4.1 grams of $Cu(NO_3)_2 \cdot 2.5H_2O$ (ALDRICH 12837) taken in 20 mL de-ionized water. The resulting material was placed on a hot plate to remove excess water and was further dried in hot air oven at 120° C. The resulting impregnated alumina was calcined by heating in air at 800° C. for 12 hours to form a copper aluminate support. Based on the starting weights of the copper salt and alumina the copper aluminate support calculated to contain 10% CuO (w/w) and 90% $Al_2O_3$ (w/w), which is designated as $10CuAl_2O_4$. Subsequently, this $10CuAl_2O_4$ was impregnated with 22 grams of $Cu(NO_3)_2 \cdot 2.5H_2O$ taken in 20 mL de-ionized water. The resulting material was placed on a hot plate to remove excess solvent and further dried in a hot air oven at 120° C. The resulting impregnated copper aluminate support was heated in air at 500° C. for 4 hours to form a copper aluminate supported copper spinel catalyst. Based on the starting weights of the copper salt and support, the composition of said spinel catalyst sample 1(a) was calculated to be 30% Cu and 70% $10CuAl_2O_4$ and was designated spinel catalyst 1(a) $30Cu/10CuAl_2O_4$.

The activity of this spinel catalyst sample 1(a) was evaluated in a fixed bed reactor. In this experiment, 0.92 grams (5.5" bed length) of spinel catalyst sample 1(a) was reduced by heating at 500° C. under 100 sccm $H_2$ for 3-4 hours. The resulting reduced catalyst sample was then treated in $H_2$ and $SiCl_4$ for 15 min at 750° C. by bubbling $H_2$ through the stainless steel $SiCl_4$ bubbler described above. The total flow of $H_2$ and $SiCl_4$ was 150 sccm, and the mole ratio of $H_2$ to $SiCl_4$ was 1:1. The $SiCl_4$ flow was controlled by $H_2$ flow by keeping the bubbler temperature at 37.2° C. The gas and vapor leaving the bubbler was fed into the glass tube of a flow reactor containing the sample 1(a) to form a reactant comprising 20% Si. After 15 minutes, the $SiCl_4$ flow was ceased and a hydrogen flow of 100 sccm was maintained while cooling to 300° C. over a period of 1 hour. When the reactor reached 300° C., $H_2$ was purged from the reactor with an argon flow of 50 sccm for 30 min. After 30 min, the argon flow was ceased, and $CH_3Cl$ was fed through the reactor at a flow rate of 5 sccm, 300° C. and atmospheric pressure for 60 min. The reactor effluent was periodically sampled and analyzed by GC to determine the weight percent of $(CH_3)_2SiCl_2$ and other chlorosilanes based on the total mass leaving the reactor. Next, the $CH_3Cl$ feed was ceased, and the (spent) reactant was treated with $H_2$ at 500° C. for 30-60 min and contacted again with $H_2/SiCl_4$ for 15 min at 750° C. to reform the reactant. The combined flow rate of $H_2$ and $SiCl_4$ was 150 sccm, and the mole ratio of $H_2$ to $SiCl_4$ was 1:1. After the reactant was reformed, the reactor was purged with argon, again, and $CH_3Cl$ was contacted with the reformed reactant as described above. The cycle was repeated for 8 times. The results are shown in Table 2. This example demonstrates that the mixture of methylchlorosilanes is produced by the method of the invention with dimethyldichlorosilane being the major product.

TABLE 2

Production of methylchlorosilanes over 30% $Cu/10CuAl_2O_4$ catalyst treated at 750° C. with $H_2/SiCl_4 = 1$ in step-1 and 5 sccm of $CH_3Cl$ at 300° C. in step-2

| Cycle (#) | Si deposited (g) | Si removed (g) | Rate* | $(CH_3)_2SiCl_2$ selectivity | $(CH_3)SiCl_3$ selectivity | Others** selectivity |
|---|---|---|---|---|---|---|
| 1 | N/A | 0.010 | 0.011 | 63% | 34% | 3% |
| 2 | 0.181 | 0.026 | 0.028 | 64% | 22% | 14% |
| 3 | 0.179 | 0.026 | 0.028 | 64% | 23% | 13% |
| 4 | 0.174 | 0.023 | 0.025 | 63% | 24% | 12% |
| 5 | 0.177 | 0.018 | 0.020 | 59% | 25% | 15% |
| 6 | N/A | 0.017 | 0.019 | 60% | 22% | 17% |
| 7 | N/A | 0.017 | 0.019 | 70% | 23% | 7% |
| 8 | 0.185 | 0.017 | 0.018 | 68% | 23% | 9% |

Rate* = g of Si/hr/g of catalyst,
Others** = $(CH_3)HSiCl_2$, $(CH_3)_2HSiCl$, $(CH_3)_3SiCl$, $SiCl_4$ To prepare sample 1(b), 12.6 grams of alumina (DAVICAT AL2720) were dried by heating at 120° C. and impregnated with 5.45 grams of $Ni(NO_3)_2 \cdot 6H_2O$ (ALDRICH 72253) taken in 20 mL de-ionized water. The resulting material was placed on a hot plate to remove excess water and was further dried in hot air oven at 120° C. The resulting impregnated alumina was calcined by heating in air at 900° C. for 12 hours to form a nickel aluminate support. Based on the starting weights of the nickel salt and alumina the nickel aluminate support was calculated to contain 10% NiO and 90% $Al_2O_3$, which was designated as $10NiAl_2O_4$. Subsequently, this $10NiAl_2O_4$ was impregnated with 22 grams of $Cu(NO_3)_2 \cdot 2.5H_2O$ taken in 20 mL de-ionized water. The resultant mixture was placed on a hot plate to remove excess water and was further dried in hot air oven at 120° C. The resulting impregnated support was heated in air at 500° C. for 4 hours to form a nickel aluminate supported copper spinel catalyst sample 1(b). Based on the starting weights of the copper salt and support the composition of said spinel catalyst sample 1(b) was calculated to be 30% Cu and 70% 10NiAl$_2$O$_4$ and was designated spinel catalyst 1(b) 30Cu/10NiAl$_2$O$_4$.

The activity of spinel catalyst sample 1(b) was evaluated in a fixed bed reactor. In this experiment, 0.9 grams (5.5" bed length) of spinel catalyst sample 1(b) was reduced under H$_2$ at 500° C. with 100 sccm for 3-4 hours then treated in H$_2$ and SiCl$_4$ for 30 min at 750° C. by bubbling H$_2$ through a stainless steel SiCl$_4$ bubbler. The total flow of H$_2$ and SiCl$_4$ was 150 sccm, and the mole ratio of H$_2$ to SiCl$_4$ of 1:1. The SiCl$_4$ flow was controlled by H$_2$ flow by keeping the bubbler temperature at 37.2° C. The gas and vapor leaving the bubbler was fed into the glass tube of a flow reactor containing the sample 1(b) to form a reactant comprising 50% Si. After 30 minutes, the SiCl$_4$ flow was ceased and a hydrogen flow of 100 sccm was maintained while cooling to 300° C. over a period of 1 hour. When the reactor reached 300° C., H$_2$ was purged from the reactor with an argon flow of 50 sccm for 30 min. After 30 min, the argon flow was ceased, and CH$_3$Cl was fed through the reactor at a flow rate of 5 sccm for 60 min at 300° C. and atmospheric pressure. The reactor effluent was periodically sampled and analyzed by GC to determine the weight percent of (CH$_3$)$_2$SiCl$_2$ and other chlorosilanes based on the total mass leaving the reactor. Next, the CH$_3$Cl feed was ceased, and the (spent) reactant was treated with H$_2$ at 500° C. for 30-60 min and contacted again with H$_2$/SiCl$_4$ for 30 min at 750° C., to reform the reactant. The combined flow rate of H$_2$ and SiCl$_4$ was 150 sccm, and the mole ratio of H$_2$ to SiCl$_4$ was 1:1. After the reactant was reformed, the reactor was purged with argon, again, and CH$_3$Cl was contacted with the reformed reactant as described above. The cycle was repeated for 4 times. The results are shown in Table 3. The example demonstrates that the mixture of methylchlorosilanes is produced by the method of the invention.

TABLE 3

Production of methylchlorosilanes over 30% Cu/10NiAl$_2$O$_4$ catalyst treated at 750° C. with H$_2$/SiCl$_4$ = 1 in step-1 and 5 sccm of CH$_3$Cl at 300° C. in step-2

| Cycle (#) | Si deposited (g) | Si removed (g) | Rate* | (CH$_3$)$_2$SiCl$_2$ selectivity | (CH$_3$)SiCl$_3$ selectivity | Others** selectivity |
|---|---|---|---|---|---|---|
| 1 | 0.463 | 0.011 | 0.012 | 31% | 54% | 15% |
| 2 | 0.419 | 0.011 | 0.012 | 35% | 44% | 21% |
| 3 | 0.412 | 0.009 | 0.010 | 37% | 38% | 25% |
| 4 | 0.407 | 0.011 | 0.012 | 28% | 42% | 31% |

Rate* = g of Si/hr/g of catalyst,
Others** = (CH$_3$)HSiCl$_2$, (CH$_3$)$_2$HSiCl, (CH$_3$)$_3$SiCl, SiCl$_4$ To prepare sample 1(c), 11.2 grams of alumina (DAVI-CAT AL2720) were dried by heating at 120° C. and impregnated with 8.2 grams of Cu(NO$_3$)$_2$.2.5H$_2$O taken in 20 mL de-ionized water. The resulting material was placed on a hot plate to remove excess water and was further dried in a hot air oven at 120° C. The resulting impregnated alumina was calcined at 800° C. in air for 12 hours to form a copper aluminate support. Based on the starting weights of the copper salt and alumina the composition of the copper aluminate support was calculated to be 20% CuO and 80% Al$_2$O$_3$, which was designated as 20CuAl$_2$O$_4$. Subsequently, this 20CuAl$_2$O$_4$ was impregnated with 9.35 grams of Cu(NO$_3$)$_2$.2.5H$_2$O taken in 20 mL de-ionized water. The resulting material was placed on a hot plate to remove excess water and was further dried in hot air oven at 120° C. The resulting impregnated material was heated at 500° C. in air for 3 hours to form a copper aluminate supported copper spinel catalyst. Based on the starting weights of the copper salt and support the final composition of said spinel catalyst sample 1(c) was calculated to be 30% Cu and 70% 20CuAl$_2$O$_4$ and was designated spinel catalyst 1(c) 30Cu/20CuAl$_2$O$_4$.

The activity of spinel catalyst sample 1(c) was evaluated in a fixed bed reactor. In this experiment, 1.15 grams (5.5" bed length) of catalyst was reduced under H$_2$ at 500° C. with 100 sccm for 3-4 hours then treated in H$_2$ and SiCl$_4$ for 15 min at 750° C. by bubbling H$_2$ through a stainless steel SiCl$_4$ bubbler. The total flow of H$_2$ and SiCl$_4$ was 150 sccm, and the mole ratio of H$_2$ to SiCl$_4$ was 1:1. The SiCl$_4$ flow was controlled by H$_2$ flow by keeping the bubbler temperature at 37.2° C. The gas and vapor leaving the bubbler was fed into the glass tube of a flow reactor containing the sample 1(c) to form a reactant comprising 20% Si. After 15 minutes, the SiCl$_4$ flow was ceased and a hydrogen flow of 100 sccm was maintained while cooling to 300° C. over a period of 1 hour. When the reactor reached 300° C., H$_2$ was purged from the reactor with an argon flow of 50 sccm for 30 min. After 30 min, the argon flow was ceased, and CH$_3$Cl was fed through the reactor at a flow rate of 5 sccm for 60 min at 300° C. and atmospheric pressure. The reactor effluent was periodically sampled and analyzed by GC to determine the weight percent of (CH$_3$)$_2$SiCl$_2$ and other chlorosilanes based on the total mass leaving the reactor. Next, the CH$_3$Cl feed was ceased, and the (spent) reactant was treated with H$_2$ at 500° C. for 30-60 min and contacted again with H$_2$/SiCl$_4$, to reform the reactant, for 15 min at 750° C. The combined flow rate of H$_2$ and SiCl$_4$ was 150 sccm, and the mole ratio of H$_2$ to SiCl$_4$ was 1:1. After the reactant was reformed, the reactor was purged with argon, again, and CH$_3$Cl was contacted with the reformed reactant as described above. The cycle was repeated for 9 times. The results are shown in Table 4. This example demonstrates that the mixture of methylchlorosilanes is produced by the method of the invention with dimethyldichlorosilane being the major product.

TABLE 4

Production of methylchlorosilanes over 30% Cu/20CuAl$_2$O$_4$ catalyst treated 750° C. with H$_2$/SiCl$_4$ = 1 in step-1 and 5 sccm of CH$_3$Cl at 300° C. in step-2

| Cycle (#) | Si deposited (g) | Si removed (g) | Rate* | (CH$_3$)$_2$SiCl$_2$ selectivity | (CH$_3$)SiCl$_3$ selectivity | Others** selectivity |
|---|---|---|---|---|---|---|
| 1 | 0.179 | 0.018 | 0.016 | 45% | 28% | 27% |
| 2 | 0.177 | 0.026 | 0.022 | 66% | 25% | 9% |
| 3 | 0.174 | 0.033 | 0.028 | 76% | 19% | 5% |
| 4 | 0.182 | 0.030 | 0.026 | 75% | 22% | 4% |
| 5 | 0.174 | 0.036 | 0.031 | 75% | 20% | 6% |
| 6 | 0.185 | 0.028 | 0.024 | 76% | 20% | 4% |
| 7 | 0.180 | 0.027 | 0.023 | 74% | 21% | 5% |
| 8 | 0.170 | 0.037 | 0.032 | 79% | 16% | 4% |
| 9 | 0.187 | 0.028 | 0.024 | 77% | 18% | 5% |

Rate* = g of Si/hr/g of catalyst,
Others** = (CH$_3$)HSiCl$_2$, (CH$_3$)$_2$HSiCl, (CH$_3$)$_3$SiCl, SiCl$_4$ In example 2, methylchlorosilanes were produced over copper aluminate type spinel catalysts treated with $H_2$ and $SiCl_4$. To prepare sample 2(a), 11.2 grams of alumina (DAVICAT AL2720) were dried by heating at 120° C. and impregnated with 8.2 grams of $Cu(NO_3)_2 \cdot 2.5H_2O$ taken in 20 mL de-ionized water. The resulting material was placed on a hot plate to remove excess water and was further dried in a hot air oven at 120° C. The resulting impregnated alumina was calcined by heating at 800° C. in air for 12 hours to form a copper aluminate spinel catalyst. Based on the starting weights of the copper salt and alumina the composition of sample 2(a) was calculated to be 20% CuO and 80% $Al_2O_3$, which was designated as spinel catalyst sample 2(a), $20CuAl_2O_4$.

The activity of spinel catalyst sample 2(a) was evaluated in a fixed bed reactor. In this experiment, 0.72 grams (5.5" bed length) of sample 2(a) was reduced under $H_2$ at 500° C. with 100 sccm for 3-4 hours then treated in $H_2$ and $SiCl_4$ for 15 min at 750° C. by bubbling $H_2$ through a stainless steel $SiCl_4$ bubbler. The total flow of $H_2$ and $SiCl_4$ was 150 sccm, and the mole ratio of $H_2$ to $SiCl_4$ was 1:1. The $SiCl_4$ flow was controlled by $H_2$ flow by keeping the bubbler temperature at 37.2° C. The gas and vapor leaving the bubbler was fed into the glass tube of a flow reactor containing the sample 2(a) to form a reactant comprising 20% Si. After 15 minutes, the $SiCl_4$ flow was ceased and a hydrogen flow of 100 sccm was maintained while cooling to 300° C. over a period of 1 hour. When the reactor reached 300° C., $H_2$ was purged from the reactor with an argon flow of 50 sccm for 30 min. After 30 min, the argon flow was ceased, and $CH_3Cl$ was fed through the reactor at a flow rate of 5 sccm for 60 min at 300° C. and atmospheric pressure. The reactor effluent was periodically sampled and analyzed by GC to determine the weight percent of $(CH_3)_2SiCl_2$ and other chlorosilanes based on the total mass leaving the reactor. Next, the $CH_3Cl$ feed was ceased, and the (spent) reactant was treated with $H_2$ at 500° C. for 30-60 min and contacted again with $H_2/SiCl_4$ for 15 min at 750° C., to reform the reactant. The combined flow rate of $H_2$ and $SiCl_4$ was 150 sccm, and the mole ratio of $H_2$ to $SiCl_4$ was 1:1. After the reactant was reformed, the reactor was purged with argon, again, and $CH_3Cl$ was contacted with the reformed reactant as described above. The cycle was repeated 4 times. The results are shown in Table 5. The example demonstrates that a mixture of methylchlorosilanes is produced by the method of the invention with dimethyldichlorosilane being the major product.

TABLE 5

Production of methylchlorosilanes over 20% $CuAl_2O_4$ catalyst treated at 750° C. with $H_2/SiCl_4 = 1$ in step-1 and 5 sccm of $CH_3Cl$ at 300° C. in step-2

| Cycle (#) | Si deposited (g) | Si removed (g) | Rate* | $(CH_3)_2SiCl_2$ selectivity | $(CH_3)SiCl_3$ selectivity | Others** selectivity |
|---|---|---|---|---|---|---|
| 1 | 0.173 | 0.015 | 0.021 | 81% | 14% | 5% |
| 2 | 0.172 | 0.015 | 0.021 | 82% | 12% | 6% |
| 3 | 0.169 | 0.018 | 0.025 | 85% | 10% | 6% |
| 4 | 0.174 | 0.018 | 0.025 | 85% | 11% | 4% |

Rate* = g of Si/hr/g of catalyst,
Others** = $(CH_3)HSiCl_2$, $(CH_3)_2HSiCl$, $(CH_3)_3SiCl$, $SiCl_4$ A spinel catalyst sample 2(b) was prepared as described above for sample 2(a), except 7 grams of alumina and 11 grams of $Cu(NO_3)_2 \cdot 2.5H_2O$ were used, and calcining was performed by heating at 1000° C. in air for 6 hours. Based on the starting weights of the copper salt and alumina the composition of sample 2(b) was calculated to be 30% CuO and 70% $Al_2O_3$, which was designated as spinel catalyst sample 2(b), $30CuAl_2O_4$.

The activity of spinel catalyst sample 2(b) was evaluated as described above for sample 2(a), except 1.25 grams of sample 2(b) was reduced under $H_2$ then treated in $H_2$ and $SiCl_4$ for 16 min at 750° C. After 16 minutes, the $SiCl_4$ flow was ceased and a hydrogen flow of 100 sccm was maintained while cooling to 320° C. over a period of 1 hour. When the reactor reached 320° C., $H_2$ was purged from the reactor with an argon flow of 50 sccm for 30 min. After 30 min, the argon flow was ceased, and $CH_3Cl$ was fed through the reactor at a flow rate of 5 sccm for 60 min at 320° C. and atmospheric pressure. The reactor effluent was periodically sampled and analyzed by GC to determine the weight percent of $(CH_3)_2SiCl_2$ and other chlorosilanes based on the total mass leaving the reactor. Next, the $CH_3Cl$ feed was ceased, and the (spent) reactant was treated with $H_2$ at 500° C. for 30-60 min and contacted again with $H_2/SiCl_4$ for 16 min at 750° C. to reform the reactant. After the reactant was reformed, the reactor was purged with argon, again, and $CH_3Cl$ was contacted with the reformed reactant as described above. The cycle was repeated 9 times. The results are shown in Table 6. This example demonstrates that a mixture of methylchlorosilanes is produced by the method of the invention with dimethyldichlorosilane being the major product.

TABLE 6

Production of methylchlorosilanes over 30% $CuAl_2O_4$ catalyst treated at 750° C. with $H_2/SiCl_4 = 1$ in step-1 and 5 sccm of $CH_3Cl$ at 320° C. in step-2

| Cycle (#) | Si deposited (g) | Si removed (g) | Rate* | $(CH_3)_2SiCl_2$ selectivity | $(CH_3)SiCl_3$ selectivity | Others** selectivity |
|---|---|---|---|---|---|---|
| 1 | 0.263 | 0.041 | 0.033 | 77% | 17% | 5% |
| 2 | 0.248 | 0.047 | 0.037 | 82% | 14% | 4% |
| 3 | 0.265 | 0.034 | 0.027 | 80% | 15% | 5% |
| 4 | 0.273 | 0.036 | 0.029 | 79% | 16% | 5% |
| 5 | 0.189 | 0.045 | 0.036 | 81% | 15% | 4% |
| 6[a] | N/A | 0.060 | 0.048 | 80% | 15% | 5% |
| 7 | 0.256 | 0.045 | 0.036 | 82% | 14% | 4% |
| 8 | 0.251 | 0.034 | 0.027 | 81% | 15% | 5% |
| 9 | 0.249 | 0.044 | 0.035 | 82% | 14% | 4% |

Rate* = g of Si/hr/g of catalyst, a) Step 1 was carried out for 36 mi,
Others** = $(CH_3)HSiCl_2$, $(CH_3)_2HSiCl$, $(CH_3)_3SiCl$, $SiCl_4$ Sample 2(c), designated $Au-Mg-CuAl_2O_4$, was prepared as described above for sample 2(b), except 3.31 grams of $CuCl_2$ (Aldrich 451665, 99.995+%), 0.077 grams $AuCl_3$ (Aldrich 334049, 99%) and 0.066 grams of $MgCl_2$ (Alfa Aesar 232-094-6, 100%) were dissolved in 35 mL concentrated HCl and heated gently for 5 min at 100° C. to form a salt solution. This salt solution was then added to 7 grams of alumina (DAVICAT AL2720), which had been previously dried by heating at 120° C. The resulting material was dried and calcined as described above for sample 2(b). Based on the starting weights of the metal precursors the loading on the alumina support was calculated to be 0.71% Au, 0.24% Mg and 22.3% Cu which was designated as spinel catalyst sample 2(c), $Au-Mg-CuAl_2O_4$.

The activity of spinel catalyst sample 2(c) was evaluated in a fixed bed reactor as described above for sample 2(b), except 0.7 grams of sample 2(c) was reduced under $H_2$ at 100 sccm at 500° C. for 3 hours and at 750° C. for 1 hour before being treated in $H_2$ and $SiCl_4$ for 10-30 min at 750° C. The remaining conditions were as described above for sample 2(b). The results are shown in Table 7. The example demonstrates that the mixture of methylchlorosilanes is produced by the method of the invention with dimethyldichlorosilane being the major product.

TABLE 7

Production of methylchlorosilanes over Au—Mg—CuAl$_2$O$_4$: catalyst treated at 750° C. with H$_2$/SiCl$_4$ = 1 in step-1 and 5 sccm of CH$_3$Cl at 320° C. in step-2

| Cycle | Step 1/min | Si dep (g) | Si rem (g) | Rate 1 | (CH$_3$)$_2$SiCl$_2$ selectivity | (CH$_3$)SiCl$_3$ selectivity | Others selectivity |
|---|---|---|---|---|---|---|---|
| 1 | 10 | 0.125 | 0.024 | 0.05 | 84% | 9% | 8% |
| 2 | 10 | 0.126 | 0.041 | 0.08 | 86% | 7% | 7% |
| 3 | 10 | 0.127 | 0.031 | 0.06 | 65% | 5% | 29% |
| 4 | 10 | 0.127 | 0.028 | 0.05 | 80% | 7% | 13% |
| 5 | 15 | 0.177 | 0.020 | 0.04 | 81% | 10% | 9% |
| 6 | 15 | N/A | N/A | N/A | N/A | N/A | N/A |
| 7 | 15 | 0.183 | 0.040 | 0.08 | 72% | 6% | 21% |
| 8 | 30 | 0.389 | 0.046 | 0.09 | 68% | 5% | 27% |
| 9 | 30 | 0.388 | 0.041 | 0.08 | 61% | 6% | 33% |

A spinel catalyst sample 2(d), designated, 13% CuO—Al$_2$O$_3$, was made from a commercially available CuO on Al$_2$O$_3$ catalyst purchased from Sigma-Aldrich (417971) by heating in a hot air oven at 500° C. for 15 hours and calcining in air at 1000° C. for 8 hours to form a copper aluminate type spinel catalyst, which was designated as 13CuAl$_2$O$_4$.

The activity of sample 2(d) was evaluated in a fixed bed reactor. In this experiment, 1.3 grams (5.5" bed length) of catalyst was reduced under H$_2$ at 500° C. with 100 sccm for 3-4 hours then treated in H$_2$ and SiCl$_4$ for 16-30 min at 750° C. by bubbling H$_2$ through a stainless steel SiCl$_4$ bubbler. The total flow of H$_2$ and SiCl$_4$ was 150 sccm, and the mole ratio of H$_2$ to SiCl$_4$ was 1:1. The SiCl$_4$ flow was controlled by H$_2$ flow by keeping the bubbler temperature at 37.2° C. The gas and vapor leaving the bubbler was fed into the glass tube of a flow reactor containing the sample 2(d) to form a reactant comprising 20-30% Si. After this, the SiCl$_4$ flow was ceased and a hydrogen flow of 100 sccm was maintained while cooling to 320° C. over a period of 1 hour. When the reactor reached 320° C., H$_2$ was purged from the reactor with an argon flow of 50 sccm for 30 min. After 30 min, the argon flow was ceased, and CH$_3$Cl was fed through the reactor at a flow rate of 5 sccm for 60 min at 320° C. and atmospheric pressure. The reactor effluent was periodically sampled and analyzed by GC to determine the weight percent of (CH$_3$)$_2$SiCl$_2$ and other chlorosilanes based on the total mass leaving the reactor. Next, the CH$_3$Cl feed was ceased, and the (spent) reactant was treated with H$_2$ at 500° C. for 30-60 min and contacted again with H$_2$/SiCl$_4$ for 16 min at 750° C. to reform the reactant. The combined flow rate of H$_2$ and SiCl$_4$ was 150 sccm, and the mole ratio of H$_2$ to SiCl$_4$ was 1:1. After the reactant was reformed, the reactor was purged with argon, again, and CH$_3$Cl was contacted with the reformed reactant as described above. The cycle was repeated for 5 times. The results are shown in Table 8. The example demonstrates that the mixture of methylchlorosilanes is produced by the method of the invention with dimethyldichlorosilane being the major product.

TABLE 8

Production of methylchlorosilanes over 13CuAl$_2$O$_4$ catalyst treated at 750° C. with H$_2$/SiCl$_4$ = 1 in step-1 and 5 sccm of CH$_3$Cl at 320° C. in step-2

| Cycle (#) | Step 1 time (min) | Si deposited (g) | Si removed (g) | Rate* | (CH$_3$)$_2$SiCl$_2$ selectivity | (CH$_3$)SiCl$_3$ selectivity | Others** selectivity |
|---|---|---|---|---|---|---|---|
| 1 | 16 | 0.228 | 0.017 | 0.015 | 63% | 31% | 6% |
| 2 | 16 | 0.231 | 0.029 | 0.027 | 76% | 13% | 11% |
| 3 | 16 | 0.231 | 0.018 | 0.014 | 76% | 17% | 7% |
| 4 | 30 | 0.383 | 0.021 | 0.016 | 73% | 17% | 10% |
| 5 | 30 | 0.383 | 0.017 | 0.013 | 66% | 15% | 19% |

Rate* = g of Si/hr/g of catalyst,
Others** = (CH$_3$)HSiCl$_2$, (CH$_3$)$_2$HSiCl, (CH$_3$)$_3$SiCl, SiCl$_4$ To prepare spinel catalyst sample 2(e), designated 43.8% CuAl$_2$O$_4$, 11.24 grams of alumina (DAVICAT AL2720) were dried by heating at 120° C. and impregnated with 14 grams of Cu(NO$_3$)$_2$.2.5H$_2$O taken in 20 mL de-ionized water. The resulting material was dried as described above for sample 2(a) by heating at 500° C. for 14 hours. The resulting material prepared as above was impregnated with 12 grams of Cu(NO$_3$)$_2$.2.5H$_2$O taken in 20 mL de-ionized water. The resulting mixture was dried by heating on a hot plate to remove excess water and further dried in a hot air oven at 120° C. The resulting impregnated alumina was heated in air at 500° C. for 16 hours, and calcined by heating at 1000° C. in air to form a copper aluminate type spinel catalyst sample 2(e). Based on the starting weights of the copper salt and alumina the final composition of sample 2(e) was calculated to be 43.8% CuO and 56.2% Al$_2$O$_3$, which is 50:50 mol % of CuO:Al$_2$O$_3$. This catalyst was analyzed by XRD, which confirmed the presence of copper aluminate spinel. A 43.8% CuAl$_2$O$_4$ spinel catalyst was formed in this example.

The activity of sample 2(e) was evaluated in a fixed bed reactor. In this experiment, 1.7 grams (5.5" bed length) of catalyst was reduced under H$_2$ at 500° C./3 hours and 750°

C./1 hour with 100 sccm then treated in $H_2$ and $SiCl_4$ for 5-60 min at 750° C. by bubbling $H_2$ through a stainless steel $SiCl_4$ bubbler. The total flow of $H_2$ and $SiCl_4$ was 150 sccm with varying $H_2$ to $SiCl_4$ mole ratio. The $SiCl_4$ flow was controlled by $H_2$ flow by varying the bubbler temperature. The gas and vapor leaving the bubbler was fed into the glass tube of a flow reactor containing sample 2(c) to form a reactant comprising 25% Si. After this, the $SiCl_4$ flow was ceased and a hydrogen flow of 100 sccm was maintained while cooling to 300° C. over a period of 1 hour. When the reactor reached 300° C., $H_2$ was purged from the reactor with an argon flow of 50 sccm for 30 min. After 30 min, the argon flow was ceased, and $CH_3Cl$ was fed through the reactor at a flow rate of 5 sccm for 40-60 min at 320° C. and atmospheric pressure. The reactor effluent was periodically sampled and analyzed by GC to determine the weight percent of $(CH_3)_2SiCl_2$ and other chlorosilanes based on the total mass leaving the reactor. Next, the $CH_3Cl$ feed was ceased, and the (spent) reactant was treated with $H_2$ at 500° C. for 30-60 min and contacted again with $H_2/SiCl_4$ at 750° C., to reform the reactant. The combined flow rate of $H_2$ and $SiCl_4$ was 150 sccm, and the mole ratio of $H_2$ to $SiCl_4$ was 1:1/2:1. After the reactant was reformed, the reactor was purged with argon, again, and $CH_3Cl$ was contacted with the reformed reactant as described above. The cycle was repeated 6 times. The results are shown in Tables 9-10. The example demonstrates that the mixture of methylchlorosilanes is produced by the method of the invention with dimethyldichlorosilane being the major product.

TABLE 9

Production of methylchlorosilanes over 43.8% $CuAl_2O_4$ catalyst treated at 750° C. with $H_2/SiCl_4$ = 1 in step-1 for 30 min and 5 sccm of $CH_3Cl$ at 320° C. in step-2 for 1 hour

| Cycle (#) | Si deposited (g) | Si removed (g) | Rate* | $(CH_3)_2SiCl_2$ selectivity | $(CH_3)SiCl_3$ selectivity | Others** selectivity |
|---|---|---|---|---|---|---|
| 1 | 0.443 | 0.052 | 0.031 | 79% | 16% | 5% |
| 2 | 0.421 | 0.054 | 0.032 | 81% | 15% | 4% |
| 3 | 0.420 | 0.056 | 0.033 | 83% | 13% | 5% |
| 4 | 0.411 | 0.061 | 0.036 | 83% | 12% | 5% |
| 5 | 0.420 | 0.058 | 0.034 | 83% | 13% | 5% |
| 6 | 0.412 | 0.055 | 0.033 | 82% | 14% | 4% |

Rate* = g of Si/hr/g of catalyst,
Others** = $(CH_3)HSiCl_2$, $(CH_3)_2HSiCl$, $(CH_3)_3SiCl$, $SiCl_4$

TABLE 10

Production of methylchlorosilanes over 43.8% $CuAl_2O_4$ catalyst treated at 750° C. in step-1 and 5 sccm of $CH_3Cl$ at 320° C. in step-2

| | $H_2/SiCl_4$ = 1 | | $H_2/SiCl_4$ = 2 | |
|---|---|---|---|---|
| Stp1 time, min | Si removed (g) | $(CH_3)_2SiCl_2$ selectivity (%) | Si removed (g) | $Me_2SiCl_2$ selectivity (%) |
| 1 | N/A | N/A | 0.001 | 23% |
| 5 | 0.015 | 65% | 0.011 | 65% |
| 10 | 0.023 | 72% | 0.019 | 73% |
| 15 | 0.033 | 77% | 0.032 | 81% |
| 30 | 0.046 | 84% | 0.045 | 82% |
| 60 | 0.054 | 82% | N/A | N/A |

In example 3, a commercially available spinel catalyst was used. A copper iron oxide ($CuFe_2O_4$) spinel catalyst purchased from Sigma-Aldrich was pelletized into 5×5 size tablets using a hydraulic press, and sieved in to 1 mm particles. The activity of this spinel catalyst was evaluated in a fixed bed reactor. In this experiment, 1.75 grams (5.5" bed length, 1 mm particles) of catalyst was reduced under $H_2$ at 500° C. with 100 sccm for 3-4 hours then treated in $H_2$ and $SiCl_4$ for 30 min at 750° C. by bubbling $H_2$ through a stainless steel $SiCl_4$ bubbler. The total flow of $H_2$ and $SiCl_4$ was 150 sccm and the mole ratio of $H_2$ to $SiCl_4$ was 1:1. The $SiCl_4$ flow was controlled by $H_2$ flow by keeping the bubbler temperature at 37.2° C. The gas and vapor leaving the bubbler was fed into the glass tube of a flow reactor containing the spinel catalyst to form a reactant comprising 20% Si. After this, the $SiCl_4$ flow was ceased, and a hydrogen flow of 100 sccm was maintained while cooling to 320° C. over a period of 1 hour. When the reactor reached 320° C., $H_2$ was purged from the reactor with an argon flow of 50 sccm for 30 min. After 30 min, the argon flow was ceased, and $CH_3Cl$ was fed through the reactor at a flow rate of 5 sccm for 60 min at 320° C. and atmospheric pressure. The reactor effluent was periodically sampled and analyzed by GC to determine the weight percent of $(CH_3)_2SiCl_2$ and other chlorosilanes based on the total mass leaving the reactor. Next, the $CH_3Cl$ feed was ceased, and the (spent) reactant was treated with $H_2$ at 500° C. for 30-60 min and contacted again with $H_2/SiCl_4$ for 30 min at 750° C., to reform the reactant. The combined flow rate of $H_2$ and $SiCl_4$ was 150 sccm, and the mole ratio of $H_2$ to $SiCl_4$ was 1:1. After the reactant was reformed, the reactor was purged with argon, again, and $CH_3Cl$ was contacted with the reformed reactant as described above. The cycle was repeated 5 times. The results are shown in Table 11. The example demonstrates that the mixture of methylchlorosilanes is produced by the method of the invention.

TABLE 11

Production of methylchlorosilanes over copper iron oxide ($CuFe_2O_4$) type spinel catalyst treated at 750° C. with $H_2/SiCl_4$ = 1 in step-1 and 5 sccm of $CH_3Cl$ at 320° C. in step-2

| Cycle (#) | $(CH_3)_2SiCl_2$ selectivity | $(CH_3)SiCl_3$ selectivity | Others** selectivity |
|---|---|---|---|
| 1 | 12% | 79% | 9% |
| 2 | 14% | 59% | 26% |
| 3 | 22% | 68% | 9% |
| 4 | 15% | 73% | 12% |
| 5 | 26% | 61% | 12% |

Others** = $(CH_3)HSiCl_2$, $(CH_3)_2HSiCl$, $(CH_3)_3SiCl$, $SiCl_4$

In example 4, a copper chromate ($2CuO.Cr_2O_3$) spinel purchased from Sigma-Aldrich was pelletized in to 5×5 size tablets using a hydraulic press, and then sieved in to 1 mm particles.

The activity of this catalyst was evaluated in a fixed bed reactor. In this experiment, 1.5 grams (5.5" bed length, 1 mm particles) of spinel catalyst was reduced under $H_2$ at 500° C. with 100 sccm for 3-4 hours then treated in $H_2$ and $SiCl_4$ for 30 min at 750° C. by bubbling $H_2$ through a stainless steel $SiCl_4$ bubbler. The total flow of $H_2$ and $SiCl_4$ was 150 sccm, and the mole ratio of $H_2$ to $SiCl_4$ was 1:1. The $SiCl_4$ flow was controlled by $H_2$ flow by keeping the bubbler temperature at 37.2° C. The gas and vapor leaving the bubbler was fed into the glass tube of a flow reactor containing the spinel catalyst to form a reactant comprising 30% Si. After step 1, the $SiCl_4$ flow was ceased and a hydrogen flow of 100 sccm was maintained while cooling to 320° C. over a period of 1 hour. When the reactor reached 320° C., $H_2$ was purged from the reactor with an argon flow of 50 sccm for 30 min. After 30 min, the argon flow was ceased, and $CH_3Cl$ was fed through the reactor at a flow rate of 5 sccm for 60 min at 320° C. and atmospheric pressure. The reactor effluent was periodically sampled and analyzed by GC to determine the weight percent of $(CH_3)_2SiCl_2$ and other chlorosilanes based on the total mass leaving the reactor. Next, the $CH_3Cl$ feed was ceased, and the (spent) reactant was treated with $H_2$ at 500° C. for 30-60 min and contacted again with $H_2/SiCl_4$, to reform the reactant, for 30 min at 750° C. The combined flow rate of $H_2$ and $SiCl_4$ was 150 sccm, and the mole ratio of $H_2$ to $SiCl_4$ was 1:1. After the reactant was reformed, it was purged with argon, again, and $CH_3Cl$ was contacted with the reformed reactant as described above. The cycle was repeated 6 times. The results are shown in Table 12. The example demonstrates that the mixture of methylchlorosilanes is produced by the method of the invention.

TABLE 12

Production of methylchlorosilanes over copper chromate (2CuO•$Cr_2O_3$) type spinel catalyst treated at 750° C. with $H_2/SiCl_4$ = 1 in step-1 and 5 sccm of $CH_3Cl$ at 320° C. in step-2

| Cycle (#) | $(CH_3)_2SiCl_2$ selectivity | $(CH_3)SiCl_3$ selectivity | Others** selectivity |
|---|---|---|---|
| 1 | 21% | 78% | 1% |
| 2 | 29% | 62% | 9% |
| 3 | 45% | 43% | 12% |
| 4 | 48% | 25% | 27% |
| 5 | 51% | 27% | 22% |
| 6 | 45% | 31% | 24% |

Others** = $(CH_3)HSiCl_2$, $(CH_3)_2HSiCl$, $(CH_3)_3SiCl$, $SiCl_4$

In example 5, copper aluminate spinel catalyst (43.8% $CuAl_2O_4$, 70 micron particle size) was loaded in to a 2 inch inner diameter quartz (inside and Inconel 600) fluidized bed reactor with 80 cm freeboard height. The catalyst was reduced under 50 vol % $N_2$ and 50 vol % $H_2$ flowing through a silica frit distributor at 500° C. for 2 hours and 750° C. for 1 hour. The reactor had a provision to feed separate $SiCl_4$ flow. The $SiCl_4$ line was preheated before feeding to the reactor, and the line was from the bottom of the reactor. After the reduction, the $N_2$ flow was ceased and the spinel catalyst was treated with $SiCl_4$ and $H_2$ for 2 hours to form a reactant comprising 5% Si. The total flow of $H_2$ and $SiCl_4$ was 15 fpm, and the mole ratio of $H_2$ to $SiCl_4$ was 1:1. The $SiCl_4$ feed rate was controlled by peristaltic pump, which was confirmed by the weight loss of the feed tank. After 2 hours, the $SiCl_4$ flow was ceased and a hydrogen flow of 0.82 LPM was maintained while cooling to 320° C. over a period of 1 hour. When the reactor reached 320° C., $H_2$ was purged from the reactor with nitrogen flow for 30 min. After 30 min, the nitrogen flow was ceased, and $CH_3Cl$ was fed through the reactor at a flow rate of 0.28 LPM diluted with nitrogen at a flow rate of 2.56 LPM for 60 min at 320° C. and atmospheric pressure. The reactor effluent was periodically sampled and analyzed by GC to determine the weight percent of $(CH_3)_2SiCl_2$ and other chlorosilanes based on the total mass leaving the reactor. Next, the $CH_3Cl$ feed was ceased, and the (spent) reactant was treated with $H_2$ at 500° C. for 30-60 min and contacted again with $H_2/SiCl_4$ for 2 hours at 750° C., to reform the reactant. The combined flow rate of $H_2$ and $SiCl_4$ was 15 fpm, and the mole ratio of $H_2$ to $SiCl_4$ was 1:1. After the reactant was reformed, the reactor was purged with nitrogen, again, and $CH_3Cl$ (diluted with nitrogen) was contacted with the reformed reactant as described above. The cycle was repeated 5 times. The results are shown in Table 13. The example demonstrates that the mixture of methylchlorosilanes is produced by the method of the invention.

TABLE 13

Production of methylchlorosilanes over 43.8$CuAl_2O_4$ catalyst treated at 750° C. with $H_2/SiCl_4$ = 1 in step-1 and $CH_3Cl$ at 320° C. in step-2 in fluid bed reactor

| Cycle (#) | Si deposited (g) | Si removed (g) | Rate* | $Me_2SiCl_2$ selectivity | $MeSiCl_3$ selectivity | Others selectivity |
|---|---|---|---|---|---|---|
| 1 | 6.379 | 0.151 | 0.002 | 40% | 22% | 38% |
| 2 | 6.401 | 0.164 | 0.002 | 48% | 31% | 21% |
| 3 | 6.294 | 0.234 | 0.003 | 37% | 54% | 10% |
| 4 | 6.273 | 0.259 | 0.003 | 54% | 36% | 10% |
| 5 | 6.273 | 0.235 | 0.003 | 49% | 35% | 16% |

Rate* = g of Si/hr/g of catalyst

The spinel catalysts described herein are distinct from supported copper catalysts. Without wishing to be bound by theory, it is thought that XRD patterns of $Al_2O_3$ supported CuO catalysts show signals due to CuO as all the alumina, and all the alumina was covered with a high loading of CuO concentration. In contrast, after calcination, the interaction of CuO with $Al_2O_3$ takes place yielding spinel phases ($CuAl_2O_4$) in the XRD pattern.

In example 6, the spinel catalyst was formed in situ. An amount of 100 g of a mixture of 43.8% CuO and 56.2% $Al_2O_3$ were placed in a 2 inch inner diameter quartz (inside and Inconel 600) fluidized bed reactor with 80 cm freeboard height. The reactor was purged under nitrogen ($N_2$) gas. The reactor was heated and the mixture was calcined under $N_2$ gas. The reactor temperature was increased slowly up to 800° C. with 100° C. increments and held for 3 h at 800° C. The reactor temperature was further increased to 950° C. and held for 1 h then cooled over night under $N_2$ atmosphere. $N_2$ gas flow was maintained at 10 ft/min to fluidize the mixture during the calcination. The next day, a sample was taken from the reactor and analyzed by XRD, which confirmed the presence of copper aluminate spinel.

This spinel was reduced under 50 vol % $N_2$ and 50 vol % $H_2$ with a total velocity of 10 ft/min. Initially, the reactor was turned on and set to 100° C. under 3 L/min of total gas stream and held for 6 minutes, and then temperature was increased to 800° C. with 100° C. increments and held for 30 min at each temperature and finally held for 3 h at 800° C. Total gas flow was maintained at 10 ft/min to fluidize the reactor contents during the reduction.

After the reduction described above, the $N_2$ flow was ceased and the spinel catalyst in the reactor was treated with $SiCl_4$ and $H_2$ for 2 hours to form a reactant comprising 5% Si. The total flow of $H_2$ and $SiCl_4$ was 10 ft/min with the mole ratio of $H_2$ to $SiCl_4$ of 1:1 in this step (1). After 2 hours, the $SiCl_4$ flow was ceased and a $H_2$ flow of 1.1 L/min was established while cooling to 300° C. and maintaining a velocity of 10 ft/min over a period of 1 hr. When the reactor reached 300° C., $H_2$ was purged from the reactor with $N_2$ flow for 30 min.

After 30 min, the $N_2$ flow was ceased, and $CH_3Cl$ was fed through the reactor at a flow rate of 0.98 L/min diluted with $N_2$ at a flow rate of 0.98 L/min at 300° C. and atmospheric pressure for 60 min in this step (2). The reactor effluent was periodically sampled and analyzed by GC to determine the weight percent of $(CH_3)_2SiCl_2$ and other chlorosilanes in the reaction product based on the total mass leaving the reactor.

Next, the $CH_3Cl$ feed was ceased, and the spent catalyst was treated with $H_2$ at 500° C. for 30 to 60 min and contacted again with $H_2$ and $SiCl_4$ for 2 hours at 750° C. to re-form the reactant. The combined flow rate of $H_2$ and $SiCl_4$ was 10 ft/min, and the mole ratio of $H_2$ to $SiCl_4$ was 1:1.

After the reactant was re-formed, it was purged with $N_2$ again, and $CH_3Cl$ (diluted with $N_2$) was contacted with the re-formed reactant as described above. The cycle was repeated 6 times. The results are shown in Table 14. The example demonstrates that the active copper aluminate catalyst can be produced in-situ to make mixture of methylchlorosilanes in a fluid bed reactor by the method of the invention.

TABLE 14

Production of methylchlorosilanes over in situ synthesized copper aluminate spinel catalyst treated at 750° C. with $H_2/SiCl_4 = 1$ in step (1) and $CH_3Cl$ at 300° C. in step (2) in a fluidized bed reactor

| Cycle (#) | Si deposited (g) | Si removed (g) | Rate* | $Me_2SiCl_2$ selectivity (%) | $MeSiCl_3$ selectivity (%) | Others selectivity (%) |
|---|---|---|---|---|---|---|
| 1 | nd | nd | nd | nd | Nd | nd |
| 2 | 9.70 | 0.02 | 0.0004 | 23 | 36 | 41 |
| 3 | 9.22 | 0.09 | 0.002 | 19 | 24 | 58 |
| 4 | 7.78 | 0.06 | 0.0013 | 47 | 51 | 2 |
| 5 | 21.23 | 0.10 | 0.002 | 30 | 19 | 51 |
| 6 | nd | nd | nd | nd | Nd | nd |

Rate* = g of Si/hr/g of reactant,
Others = combined amounts of $MeHSiCl_2$, $Me_2HSiCl$, $Me_3SiCl$, and $SiCl_4$;
nd = not measured In example 7, CuO and $Al_2O_3$ (3 g total, 1:1 mole ratio) were mixed and placed in a ½" quartz reactor (inside Inconel 600). The reactor was purged with $N_2$ gas and then heated to 900° C. calcined the CuO and $Al_2O_3$ mixture under $N_2$ gas flow at 50 sccm at for 8 hours. The reactor was then cooled over night under an $N_2$ atmosphere. The next day, a sample was taken from the reactor and analyzed by XRD, which confirmed the presence of copper aluminate spinel.

The copper aluminate spinel was reduced under $H_2$ gas at 500° C. for 2 h and 750° C. for 2 h with 100 sccm flow rate and then treated in $H_2$ and $SiCl_4$ for 30 min at 750° C. by bubbling $H_2$ through a stainless steel $SiCl_4$ bubbler. The total flow of $H_2$ and $SiCl_4$ was 150 sccm with the mole ratio of $H_2$ to $SiCl_4$ of 1:1. The $SiCl_4$ flow was controlled by $H_2$ flow by keeping the bubbler temperature at 37.2° C. The gas and vapor leaving the bubbler was fed into a flow reactor containing the copper aluminate spinel catalyst to form a reactant comprising 20% Si.

After 30 min, the $SiCl_4$ flow was ceased and a $H_2$ flow of 100 sccm was maintained while cooling to 300° C. over a period of 1 hour. When the reactor reached 300° C., $H_2$ was purged from the reactor with an argon flow of 50 sccm for 30 min. After 30 min, the argon flow was ceased, and $CH_3Cl$ was fed through the reactor at a flow rate of 5 sccm, 300° C. and atmospheric pressure for 60 min. The reactor effluent was periodically sampled and analyzed by GC to determine the weight percent of $(CH_3)_2SiCl_2$ and other chlorosilanes based on the total mass leaving the reactor.

Next, the $CH_3Cl$ feed was ceased, and the spent catalyst was treated with $H_2$ at 500° C. for 30 to 60 min and contacted again with $H_2$ and $SiCl_4$, for 30 min at 750° C. to re-form the reactant. The combined flow rate of $H_2$ and $SiCl_4$ was 150 sccm, and the mole ratio of $H_2$ to $SiCl_4$ was 1:1. After the reactant was re-formed, the reactor was purged with argon again, and $CH_3Cl$ was contacted with the re-formed reactant as described above. The cycle was repeated 7 times. The results are shown in Table 15. The example demonstrated that the copper aluminate spinel catalyst can be produced in situ to make a reaction product comprising mixture of methylchlorosilanes in a fixed bed reactor by the method described herein.

TABLE 15

Production of methylchlorosilanes over in situ synthesized copper aluminate spinel catalyst treated at 750° C. with $H_2/SiCl_4 = 1$ in step (1) and $CH_3Cl$ at 300° C. in step (2) in a fixed bed reactor

| Cycle (#) | Si deposited (mg) | Si removed (mg) | Rate* | $Me_2SiCl_2$ selectivity (%) | $MeSiCl_3$ selectivity (%) | Others selectivity (%) |
|---|---|---|---|---|---|---|
| 1 | 499 | 97 | 0.05 | 79 | 13 | 8 |
| 2 | 412 | 66 | 0.03 | 73 | 18 | 9 |
| 3 | 422 | 53 | 0.03 | 77 | 18 | 5 |
| 4 | 412 | 52 | 0.03 | 75 | 24 | 1 |
| 5 | 410 | 46 | 0.02 | 78 | 20 | 3 |
| 6 | 412 | 31 | 0.02 | 66 | 30 | 4 |
| 7 | 403 | 56 | 0.03 | 81 | 16 | 3 |

Rate* = g of Si/hr/g of reactant,
Others = collectively, $MeHSiCl_2$, $Me_2HSiCl$, $Me_3SiCl$, $SiCl_4$ In example 8, CuO and $Al_2O_3$ (20 g total, 1:1 mole ratio) were mixed and then placed in a flat bottom crucible. The mixture was calcined in air in an oven at 900° C. for 15 hours with 5° C./min rate of heating and then cooled over night to room temperature. The next day, a sample was taken from the reactor and analyzed by XRD, which confirmed the presence of copper aluminate spinel.

The copper aluminate spinel (2 g) was placed in a ½" quartz reactor (inside Inconel 600). The copper aluminate spinel was then used as described above in example 7, except that the cycle was repeated 3 times. The results are shown in Table 16. The example demonstrated that the copper aluminate spinel catalyst can be produced by physical mixing of CuO and $Al_2O_3$ using air calcination to make mixture of methylchlorosilanes in a fixed bed reactor by the method described herein.

TABLE 16

Production of methylchlorosilanes over air calcined copper aluminate spinel catalyst treated at 750° C. with $H_2/SiCl_4$ in step (1) and $CH_3Cl$ at 300° C. in step (2) in a fixed bed reactor

| Cycle (#) | Si deposited (mg) | Si removed (mg) | Rate* | $Me_2SiCl_2$ selectivity | $MeSiCl_3$ selectivity | Others selectivity |
|---|---|---|---|---|---|---|
| 1 | 484 | 78 | 0.038 | 82% | 13% | 5% |
| 2 | 435 | 77 | 0.038 | 85% | 11% | 3% |
| 3 | 435 | 84 | 0.041 | 81% | 11% | 8% |

Rate* = g of Si/hr/g of reactant,
Others = collectively, $MeHSiCl_2$, $Me_2HSiCl$, $Me_3SiCl$, $SiCl_4$ The disclosure of ranges includes the range itself and also anything subsumed therein, as well as endpoints. For example, disclosure of a range of 2.0 to 4.0 includes not only the range of 2.0 to 4.0, but also 2.1, 2.3, 3.4, 3.5, and 4.0 individually, as well as any other number subsumed in the range. Furthermore, disclosure of a range of, for example, 2.0 to 4.0 includes the subsets of, for example, 2.1 to 3.5, 2.3 to 3.4, 2.6 to 3.7, and 3.8 to 4.0, as well as any other subset subsumed in the range.

With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination with any other member or members of the group, and each member provides adequate support for specific embodiments within the scope of the appended claims. For example, disclosure of the Markush group: alkyl, aryl, and carbocyclic includes the member alkyl individually; the subgroup alkyl and aryl; and any other individual member and subgroup subsumed therein.

It is also to be understood that any ranges and subranges relied upon in describing various embodiments of the present disclosure independently and collectively fall within the scope of the appended claims, and are understood to describe and contemplate all ranges including whole and/or fractional values therein, even if such values are not expressly written herein. The enumerated ranges and subranges sufficiently describe and enable various embodiments of the present disclosure, and such ranges and subranges may be further delineated into relevant halves, thirds, quarters, fifths, and so on. As just one example, a range "of 200 to 1400" may be further delineated into a lower third, i.e., from 200 to 600, a middle third, i.e., from 600 to 1000, and an upper third, i.e., from 1000 to 1400, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 0.1%" inherently includes a subrange from 0.1% to 35%, a subrange from 10% to 25%, a subrange from 23% to 30%, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range of "1 to 9" includes various individual integers, such as 3, as well as individual numbers including a decimal point (or fraction), such as 4.1, which may be relied upon and provide adequate support for specific embodiments within the scope of the appended claims.

The subject matter of all combinations of independent and dependent claims, both singly and multiply dependent, is expressly contemplated but is not described in detail for the sake of brevity. The disclosure has been described in an illustrative manner, and it is to be understood that the terminology which has been used is intended to be in the nature of words of description rather than of limitation. Many modifications and variations of the present disclosure are possible in light of the above teachings, and the disclosure may be practiced otherwise than as specifically described.

The invention claimed is:

1. A method for preparing a reaction product comprising a halosilane comprises steps (1) and (2), where:
   step (1) is contacting, at a temperature from 200° C. to 1400° C., a first ingredient comprising a silane of formula $H_aR_bSiX_{(4-a-b)}$, where subscript a is an integer from 0 to 4, subscript b is 0 or 1, a quantity (a+b)≤4, each R is independently a monovalent organic group, and each X is independently a halogen atom; with a spinel catalyst comprising copper; thereby forming a reactant, with the proviso that when the quantity (a+b)<4, then the first ingredient further comprises $H_2$; and
   step (2) is contacting the reactant with a second ingredient comprising an organohalide at a temperature from 100° C. to 600° C.; thereby forming the reaction product and a spent reactant; and where the method optionally further comprises steps (3) and (4), and where
   step (3) is contacting, at a temperature from 200° C. to 1400° C., the spent reactant with an additional first ingredient comprising additional silane of formula $H_aR_bSiX_{(4-a-b)}$, where subscript a is an integer from 0 to 4, subscript b is 0 or 1, the quantity (a+b)≤4, each R is independently a monovalent organic group, and each X is independently a halogen atom, with the proviso that when the quantity (a+b)<4, then the additional ingredient further comprises $H_2$; thereby re-forming the reactant, and
   step (4) is contacting the reactant re-formed in step (3) with an additional second ingredient comprising organohalide at a temperature from 100° C. to 600° C.; thereby forming an additional reaction product and an additional spent reactant, and
   where the method optionally further comprises step (5), where step (5) is repeating steps (3) and (4) at least one time; and
   where the method optionally further comprises step (6) after any one or more of steps (2) to (5), where step (6) is recovering the halosilane.

2. The method of claim 1, where the spinel catalyst meets one of conditions (A) to (E), where
   Condition (A) is that copper is part of the spinel;
   Condition (B) is that copper is part of the spinel and the spinel catalyst further comprises excess support;
   Condition (C) is that copper is part of the spinel and the spinel catalyst further comprises a promoter;
   Condition (D) is that the spinel catalyst comprises copper supported on a spinel; or
   Condition (E) is that the spinel catalyst comprises both copper supported on a spinel and copper forming part of the spinel.

3. The method of claim 1, where the spinel catalyst comprises one or more of $CuAl_2O_4$ or $CuFe_2O_4$, 20% $CuAl_2O_4$, 30% $CuAl_2O_4$, 43.8% $CuAl_2O_4$, 13% $CuAl_2O_4$, Au—Mg—$CuAl_2O_4$, CuO/$NiAl_2O_4$, Cu/$CuAl_2O_4$, Cu/$NiAl_2O_4$, Cu/$MgAl_2O_4$, 30% Cu/10% $NiAl_2O_4$, or 2CuO.$Cr_2O_3$, CuO/$CuAl_2O_4$, 30% Cu/10% $CuAl_2O_4$ or 30% Cu/20% $CuAl_2O_4$.

4. The method of claim 1, where the spinel catalyst comprises a spinel of empirical formula $CuM'_2O_4$, where M' is Al, Cr, Fe, Mg, or Ni.

5. The method of claim 1, where the spinel catalyst is prepared by a method comprising:
   i) combining a support and a precursor, thereby forming a combination; and
   ii) calcining the combination at a temperature for a time and in an atmosphere sufficient to form the spinel catalyst.

6. The method of claim 5, further comprising: steps a) and b) before step i) and/or after step ii), where
   step a) is combining the support and an additional metal precursor, thereby forming a further combination; and
   step b) is calcining the further combination to form the spinel catalyst; wherein the metal in the metal precursor is a metal other than copper.

7. The method of claim 1, further comprising:
   purging and/or treating the spinel catalyst, before contacting the spinel catalyst with the ingredient comprising the silane in step (1); and/or
   purging and/or treating the reactant, before contacting the reactant with the organohalide in step (2); and/or purging and/or treating, the spent reactant before contacting the spent reactant with the additional ingredient in step (3); and/or purging and/or treating the reactant re-formed in step (3), before the contacting the reactant re-formed in step (3) with the (additional) organohalide in step (4); and/or purging and/or treating the additional spent reactant.

8. The method of claim 1, where the silane comprises one or more of a tetrahalosilane of formula $SiX_4$, a trihalosilane of formula $HSiX_3$, a dihalosilane of formula $H_2SiX_2$, a monohalosilane of formula $H_3SiX$, silane of formula $SiH_4$, or a combination thereof.

9. The method of claim 1, where a=0, b=0, and the silane is a tetrahalosilane of formula $SiX_4$.

10. The method of claim 1, where the organohalide has formula RX, where R is alkyl or aryl, and X is Cl.

11. The method of claim 1, where contacting the reactant with the organohalide in step (2), and optionally step (4), when present, is performed in the absence of $H_2$.

12. The method of claim 1, where the reaction product comprises a halosilane of formula $R_{(4-c)}SiX_c$, where subscript c is 1, 2, 3, or 4.

13. The method of claim 1, where the reaction product comprises a halosilane of formula $R_2SiX_2$.

14. The method of claim 12, where R is methyl and X is Cl.

15. The method of claim 1 further comprising using the halosilane as a reactant to make a polyorganosiloxane.

16. The method of claim 1, where the spinel catalyst is prepared by a method comprising:
   i) combining copper oxide and a second metal oxide, where the second metal oxide differs from copper oxide,
   ii) calcining the combination to form the spinel catalyst.

17. The method of claim 16, where step ii) is performed in a reactor, and step (1) is performed in the same reactor.

18. The method of claim 16, where the second metal oxide is selected from the group consisting of $Al_2O_3$, $Cr_2O_3$, and $Fe_2O_3$.

19. The method of claim 17, where the second metal oxide is selected from the group consisting of $Al_2O_3$, $Cr_2O_3$, and $Fe_2O_3$.

20. The method of claim 13, where R is methyl and X is Cl.

* * * * *